US010307556B2

(12) United States Patent
Bugamelli et al.

(10) Patent No.: US 10,307,556 B2
(45) Date of Patent: Jun. 4, 2019

(54) PATIENT INTERFACE DEVICES WITH ADHESIVE ATTACHNMENT

(71) Applicant: KONINKLIJKE PHILIPS N.V., Eindhoven (NL)

(72) Inventors: Antonio Bugamelli, Mars, PA (US); Jerome Matula, Jr., Apollo, PA (US); Lutz Christian Gerhardt, Eindhoven (NL); Steven Ernest Franklin, Eindheoven (NL); Harmina Christina Zeijlstra, Breda (NL); Lance Ranard Busch, Trafford, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 753 days.

(21) Appl. No.: 14/897,062

(22) PCT Filed: Jun. 10, 2014

(86) PCT No.: PCT/IB2014/062084
§ 371 (c)(1),
(2) Date: Dec. 9, 2015

(87) PCT Pub. No.: WO2014/207594
PCT Pub. Date: Dec. 31, 2014

(65) Prior Publication Data
US 2016/0114119 A1  Apr. 28, 2016

Related U.S. Application Data

(60) Provisional application No. 61/834,555, filed on Jun. 13, 2013.

(51) Int. Cl.
*A61M 16/06* (2006.01)

(52) U.S. Cl.
CPC .... *A61M 16/0688* (2014.02); *A61M 16/0622* (2014.02); *A61M 16/0666* (2013.01); *A61M 16/0633* (2014.02)

(58) Field of Classification Search
CPC .............. A61M 16/0488; A61M 16/06; A61M 16/0605; A61M 16/0622; A61M 16/0633;
(Continued)

(56) References Cited

U.S. PATENT DOCUMENTS 5,676,133 A   10/1997  Hickle
5,918,598 A *  7/1999  Belfer ................ A41D 13/1176
                                            128/205.25
(Continued)

FOREIGN PATENT DOCUMENTS

CN       101653632 A      2/2010
CN       101954139 A      1/2011
(Continued)

OTHER PUBLICATIONS

3M Technical Information Sheet, Product No. 1509, 3M Double Coated Medical Tape; retrieved from https://multimedia.3m.com/mws/media/792056O/3m-1509-dc-polyethylene-tape-tis-jun13.pdf.*

(Continued)

*Primary Examiner* — Jan Christopher L Merene
*Assistant Examiner* — Joseph D. Boecker
(74) *Attorney, Agent, or Firm* — Michael W. Haas

(57) ABSTRACT

Patient interface devices (8) structured to deliver a flow of breathing gas to an airway of a patient include a member (16) structured to contact and adhere to a face of the patient responsive to the patient interface being donned by the patient, the member having a contact surface and an adhesive layer (34) provided on the contact surface.

20 Claims, 19 Drawing Sheets

(58) Field of Classification Search
CPC .......... A61M 16/0683; A61M 16/0666; A61M 16/0688; A62B 18/084; A41D 13/1169
See application file for complete search history.

(56) References Cited

U.S. PATENT DOCUMENTS

| | | | |
|---|---|---|---|
| 6,196,223 B1 | 3/2001 | Belfer | |
| 6,341,606 B1* | 1/2002 | Bordewick | A61M 16/06 128/206.12 |
| 8,291,906 B2 | 10/2012 | Kooij | |
| 2002/0157673 A1* | 10/2002 | Kessler | A61M 16/0666 128/207.18 |
| 2005/0284479 A1 | 12/2005 | Draegerwerk | |
| 2008/0066209 A1* | 3/2008 | Kayerod | A45D 44/12 2/15 |
| 2008/0271739 A1 | 11/2008 | Facer et al. | |
| 2008/0302365 A1* | 12/2008 | Cohen | A61M 16/06 128/206.12 |
| 2010/0000534 A1* | 1/2010 | Kooij | A61M 16/0666 128/204.18 |
| 2010/0229872 A1* | 9/2010 | Ho | A61M 16/06 128/206.25 |
| 2011/0005524 A1 | 1/2011 | Veliss | |
| 2011/0067704 A1* | 3/2011 | Kooij | A61M 16/0666 128/207.18 |
| 2011/0146688 A1* | 6/2011 | Lee | A61M 16/06 128/206.25 |
| 2011/0212325 A1* | 9/2011 | Determan | A61L 15/58 428/332 |
| 2012/0006329 A1* | 1/2012 | Beevers | A61M 16/06 128/206.25 |
| 2012/0037167 A1* | 2/2012 | Quiray | A61M 16/0666 128/858 |
| 2012/0138060 A1* | 6/2012 | Barlow | A61M 16/0666 128/205.25 |
| 2012/0197173 A1* | 8/2012 | Babitz | A61F 13/0008 602/54 |
| 2012/0204881 A1 | 8/2012 | Davidson | |
| 2014/0150799 A1* | 6/2014 | Daly | A61M 16/06 128/206.25 |
| 2014/0349108 A1* | 11/2014 | Fung | C09J 7/50 428/345 |
| 2018/0296785 A1* | 10/2018 | Heatherington | A61M 16/0493 |

FOREIGN PATENT DOCUMENTS

| | | |
|---|---|---|
| JP | 2010514525 A | 5/2010 |
| JP | 2010525875 A | 7/2010 |
| WO | WO9925410 A1 | 5/1999 |
| WO | WO0050121 A1 | 8/2000 |
| WO | 2008080396 A1 | 7/2008 |
| WO | WO2009066202 A2 | 5/2009 |
| WO | 2013086146 A2 | 6/2013 |

OTHER PUBLICATIONS

Scapa Medical product brochure; retrieved from www.scapa.com/files/Scapa_NA_Medical_Brochure.pdf.*

* cited by examiner

PATIENT INTERFACE DEVICES WITH ADHESIVE ATTACHNMENT

CROSS-REFERENCE TO RELATED APPLICATIONS

This patent application claims the priority benefit under 35 U.S.C. § 371 of international patent application no. PCT/IB2014/062084, filed Jun. 10, 2014, which claims the priority benefit under 35 U.S.C. § 119(e) of U.S. Provisional Application No. 61/834,555 filed on Jun. 13, 2013, the contents of which are herein incorporated by reference.

BACKGROUND OF THE INVENTION

1. Field of the Invention

The present invention pertains to patient interface devices structured to deliver a flow of breathing gas to a patient, and, in particular, to patient interface devices employing adhesives having specific characteristics and in specific configurations to assist in securing the patient interface device to the head of the patient during use in therapy.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, a nasal cushion that rests beneath the patient's nose (such as a "pillows" style nasal cushion having nasal prongs that are received within the patient's nares or a "cradle" style nasal cushion that rests beneath and covers the patient's nares), or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

The headgear typically wraps around the patient's head (coming in contact with the patient's hair and face) in order to apply the necessary forces normal to the face to achieve a suitable seal. This application of a normal force to the face, if too strong, can result in undesirable skin irritations, such as red marks, and/or patient discomfort. Additionally, some mask configurations, such as full face or nasal masks, rely on a flap along the profile of the mask to enable a seal to be achieved along the face. Due to the uniqueness of each person's face, leak paths or mask instability can occur along the mask profile, requiring the patient to use an uncomfortable amount of force.

SUMMARY OF THE INVENTION

In one embodiment, a patient interface device structured to deliver a flow of breathing gas to an airway of a patient is provided. The patient interface device includes a member structured to contact and adhere to a face of the patient responsive to the patient interface being donned by the patient, the member having a contact surface including a base region, an apex region located opposite base region, a first side region, and a second side region located opposite the first side region, the member having an adhesive layer provided on the contact surface, wherein the adhesive layer has a pull-off strength value throughout the adhesive layer that is ≤40 kPa and an adhesive shear strength value throughout the adhesive layer that is that is ≤27 kPa, wherein a first thickness of the adhesive layer in the base region is ≥0.1 mm and ≤0.5 mm and wherein a second thickness of the adhesive layer in each of the apex region, the first side region and the second side region is ≥0.5 mm and ≤1.0 mm.

In another embodiment, a patient interface device structured to deliver a flow of breathing gas to an airway of a patient is provided that includes a nasal cushion structured to contact a nose of the patient and deliver the flow of breathing gas to the nose, and an attachment member coupled to and surrounding at least a portion of the nasal cushion, the attachment member being structured to contact and adhere to a face of the patient responsive to the patient interface being donned by the patient. The attachment member has a contact surface and an adhesive layer provided on the contact surface, wherein the adhesive layer has a pull-off strength value throughout the adhesive layer that is ≤40 kPa and an adhesive shear strength value throughout the adhesive layer that is that is ≤27 kPa, wherein a first thickness of the adhesive layer in a first region thereof is ≥0.1 mm and ≤0.5 mm and wherein a second thickness of the adhesive layer in a second region thereof is ≥0.5 mm and ≤1.0 mm.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1A:
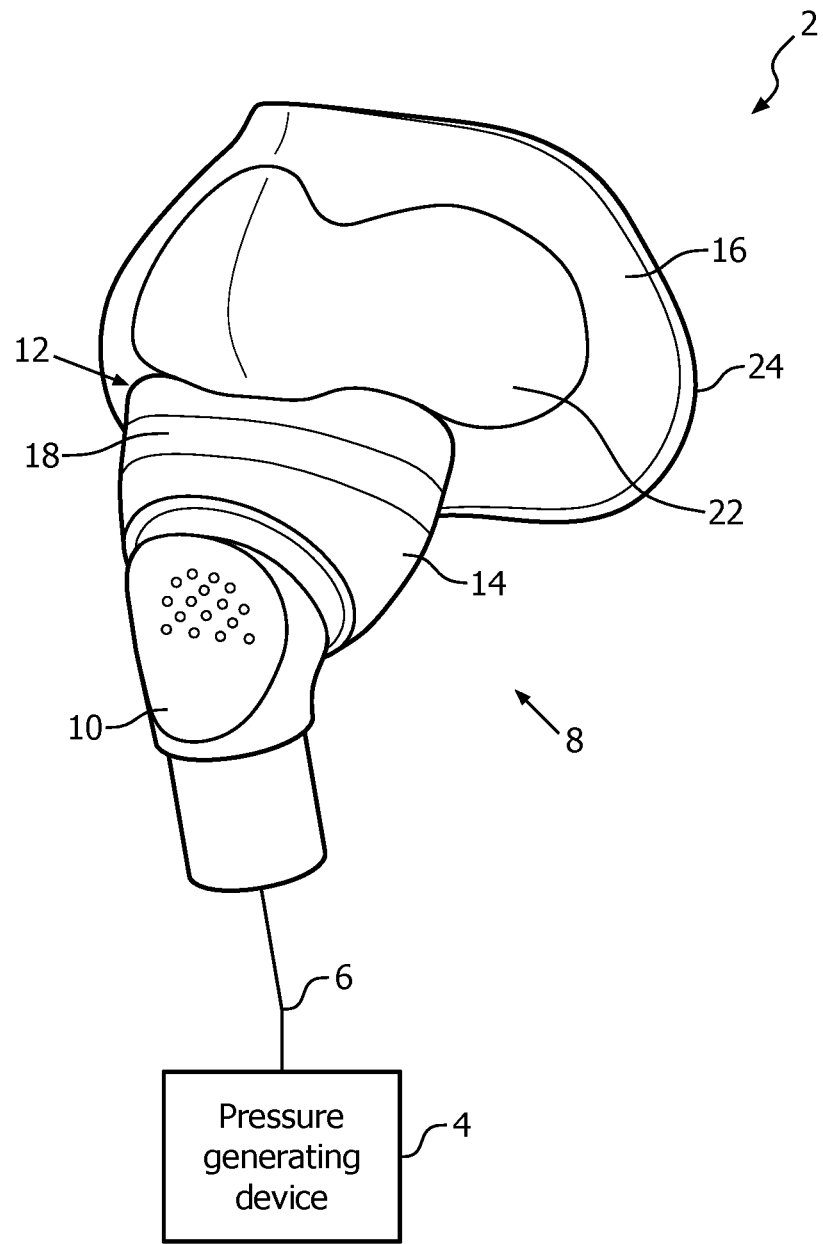
FIGS. 1A and 1B are schematic representations of a system adapted to provide a regimen of respiratory therapy to a patient according to one exemplary embodiment.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "adhesive shear strength" shall mean shear stress in kilopascals (force per unit area) of the bond between an adhesive member (e.g., a backing strip made of, for example, silicone rubber) and human skin in a certain condition (oily, dry, etc). In connection with adhesive shear strength, the shear loading is induced with a force parallel to the skin.

As used herein, the term "pull-off strength" shall mean tensile stress in kilopascals (force per unit area) of the bond between an adhesive member (e.g., a backing strip made of, for example, silicone rubber) and human skin in a certain condition (oily, dry, etc). Thus, "pull-off strength" refers to the characterized peak stress where the bond between the skin and adhesive member breaks. In connection with pull-off strength, Tensile loading is achieved by applying force in a direction perpendicular to the skin.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Figure 1B:
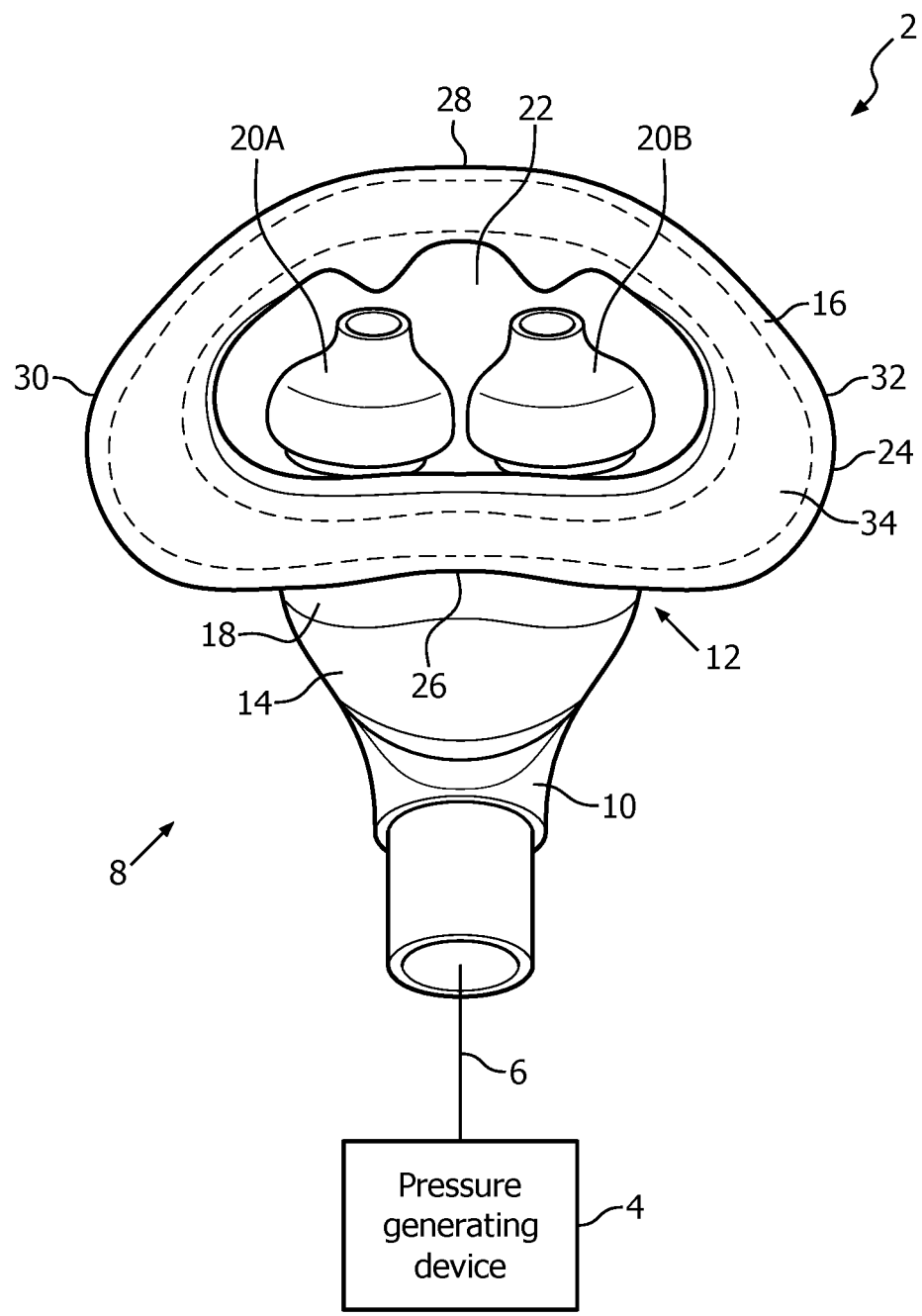

A system 2 adapted to provide a regimen of respiratory therapy to a patient according to one exemplary embodiment is generally shown in FIGS. 1A and 1B. System 2 includes a pressure generating device 4, a delivery conduit 6, and a patient interface device 8 having a fluid coupling conduit 10 (patient interface device 8 is shown in isometric view in FIG. 1A and in rear elevational view in FIG. 1B). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

As seen in FIGS. 1A and 1B, patient interface device 8 includes a patient sealing assembly 12 which facilitates the delivery of the flow of breathing gas to the airway of a patient. Patient sealing assembly 12 includes a nasal cushion 14 and a nasal sealing cover 16 coupled to nasal cushion 14.

In the illustrated embodiment, nasal cushion 14 is a "pillows" style nasal cushion made of a flexible, cushiony, elastomeric material, such as, without limitation, silicone, an appropriately soft thermoplastic elastomer, a closed cell foam, or any combination of such materials. As seen in FIGS. 1A and 1B, the exemplary pillows style nasal cushion 14 includes a main body portion 18 having nasal prongs 20A and 20B (FIG. 1B) extending from a top side thereof. Nasal prongs 20A and 20B are structured to be received within the nares of the patient. Alternatively, nasal cushion 28 may be a "cradle" style nasal cushion that rests beneath and covers the patient's nares, or some other suitable nasal cushion configuration structured to engage the nose of the patient.

FIGS. 1C, 1D, 1E and 1F are front isometric, rear elevational, bottom isometric and top elevational views, respectively, of nasal sealing cover 16. Nasal sealing cover 16 is structured to be removeably coupled to nasal cushion 14. Nasal sealing cover 16, like nasal cushion 14, is, in the exemplary embodiment, made of a flexible, cushiony, elastomeric material, such as, without limitation, silicone, an appropriately soft thermoplastic elastomer, a closed cell foam, or any combination of such materials. Nasal sealing cover 16 is also structured to surround and envelop nasal prongs 20A and 20B, and includes a central portion 22 for this purpose (ambient air surrounds the exterior of the nose underneath nasal sealing cover 16).

Figure 1C:
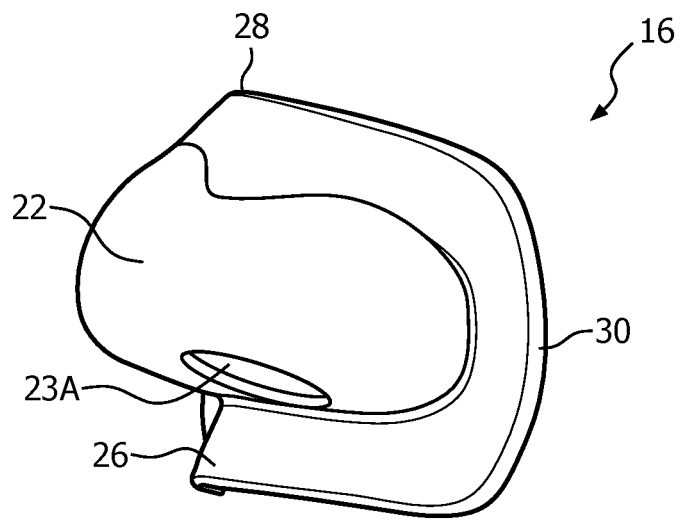
FIGS. 1C, 1D, 1E and 1F are front isometric, rear elevational, bottom isometric and top elevational views, respectively, of a nasal sealing cover forming a part of a patient interface device of the system of FIGS. 1A and 1B.
Figure 1D:
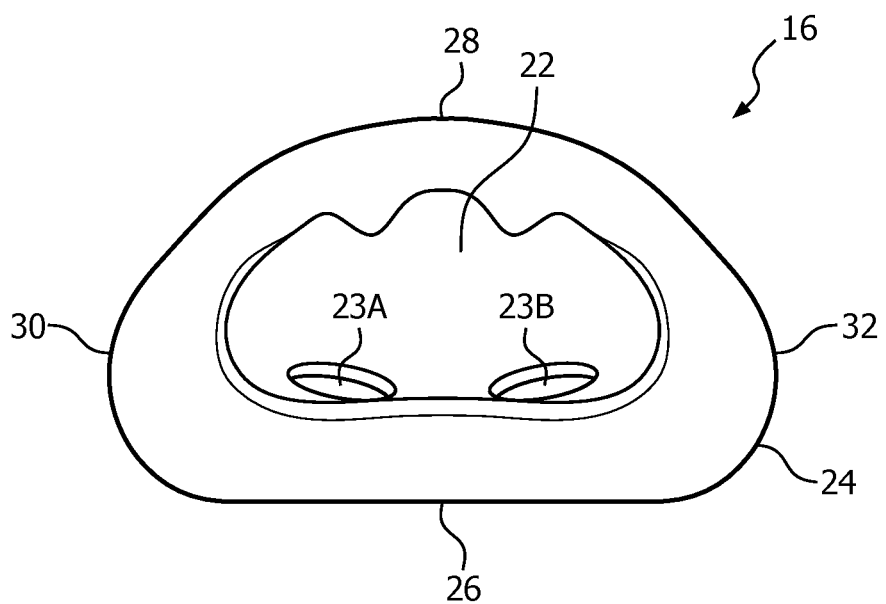
Figure 1E:
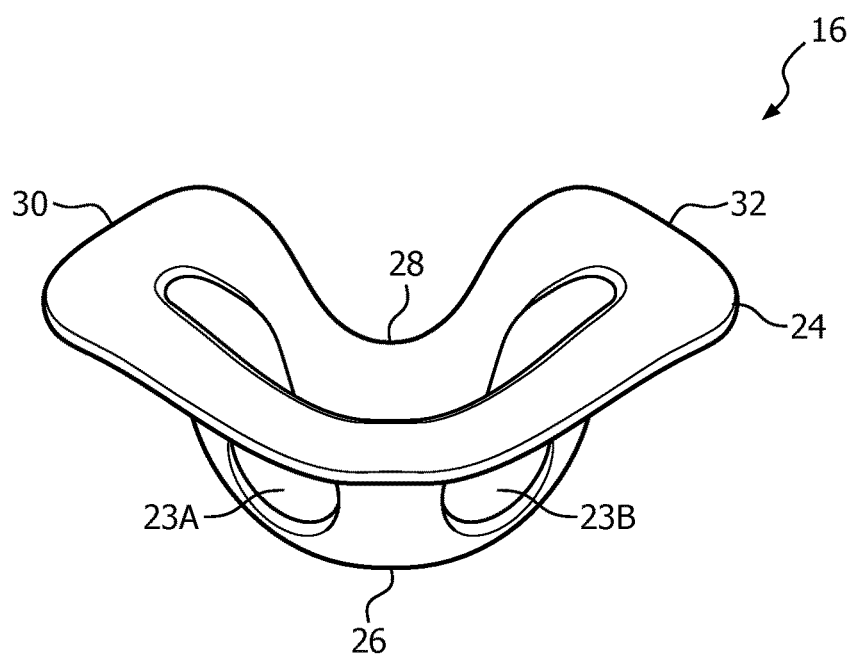
Figure 1F:
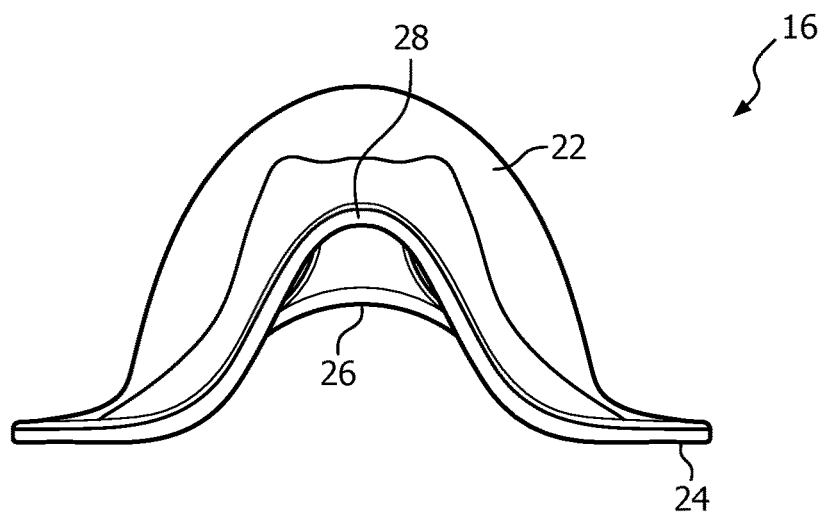

As seen in FIGS. 1C-1E, nasal sealing cover 16 includes apertures 23A and 23B for removeably receiving nasal prongs 20A and 20B. A contoured sealing edge portion 24 is coupled to and extends generally radially outwardly from central portion 22. Sealing edge portion 24 is structured to engage the patient's face when patient interface device 8 is donned by the patient to support nasal cushion 14 to the face. Sealing edge portion 24 has a generally triangular shape including a bottom/base region 26, an apex region 28 located opposite bottom region 26, a first side region 30 and a second side region 32 located opposite first side region 30. Bottom/base region 26 is structured to engage the patient's upper lip/mouth region, apex region 28 is structured to engage the patient's nose bridge region (and includes a contoured indent for that purpose), and first side region 30 and second side region 32 are structured to engage the patient's cheek region.

Patient interface device 8 of the present embodiment is structured and configured to be secured to the patient's face without the need to also use a headgear apparatus coupled to patient interface device 8. In the exemplary embodiment, up to 50 g of patient interface device may be secured in this manner. Such securing of patient interface device 8 to the face is achieved by way of an adhesive layer 34 (represented by the dotted lines in FIG. 1B, which could be continuous as shown or broken into a number of adjacent deposits) provided at/on certain portions of the inside surface of sealing edge portion 24, and relies, at least in part, on the shear force capabilities of the adhesive used in adhesive layer 34 across the area in which it is provided.

The adhesive used in adhesive layer 34 is, in the exemplary embodiment, a medical-grade and/or biocompatible adhesive and may be, for example and without limitation, a silicone based adhesive or a polyurethane based adhesive. One suitable adhesive used in adhesive layer 34 is Silpuran® 2130 sold by Wacker Chemie AG, which is a 2-part, addition-curing silicone composition curing to a soft, tacky silicone adhesive. In such an implementation, the application of Silpuran® 2130 may include no surface treatment, application of a primer, and/or application of a surface roughing to sealing edge portion 24 in the transverse direction relative to a peal pattern across the person's face (i.e., from left to right). Other suitable adhesives include, without limitation, Dow Corning® MG7-9900 and Technogel® BTGS-125AX.

In the exemplary embodiment, the adhesive and adhesive layer 34 has the particular characteristics and configurations described below (relating to adhesive shear strength, pull-off strength, layer thickness and/or peel adhesion value).

Furthermore, in an exemplary embodiment, adhesive layer 34 has the following mechanical characteristics. First, the adhesive used in adhesive layer 34 must react adhesively with human skin in a manner wherein it is able to be removeably bonded to the face while remaining cohesively bonded to the silicone or other material of nasal sealing cover 16 (to mitigate the risk of adhesive material remaining on the patient's face, all adhesive material should decouple from the skin while remaining attached to nasal sealing cover 16). Adhesive layer 34 has an area ($mm^2$) to adhesive shear strength (kPa) ratio of about 140 $mm^2$/kPa to about 270 $mm^2$/kPa, which range includes an area ($mm^2$) to adhesive shear strength (kPa) ratio of 150 determined by the present inventors to be optimal for dry skin and an area ($mm^2$) to adhesive shear strength (kPa) ratio of 257 determined by the present inventors to be optimal for oily skin.

Adhesive layer 34 has an area ($mm^2$) to pull-off strength (kPa) ratio of about 60 $mm^2$/kPa to about 105 $mm^2$/kPa, which range includes an area ($mm^2$) to pull-off strength (kPa) ratio of 66.3 determined by the present inventors to be optimal for dry skin and an area ($mm^2$) to pull-off strength (kPa) ratio of 99.5 determined by the present inventors to be optimal for oily skin. Also, the thickness of adhesive layer 34 as deposited on the inside surface of sealing edge portion 24 ranges from 0.1 mm to 1.0 mm. In particular, in the exemplary embodiment, the thickness of adhesive layer 34 in bottom/base region 26 of sealing edge portion 24 is $\geq 0.1$ mm and $\leq 0.5$ mm (for optimal adhesive shear strength), because bottom/base region 26 is structured to contact the upper lip/mouth region of the patient, which tends to have a higher concentration of oil than other parts of the face. In addition, in the exemplary embodiment, the thickness of adhesive layer 34 in apex region 28, first side region 30, and second side region 32 of sealing edge portion 24 is $\geq 0.5$ mm and $\leq 1.0$ mm, because those regions are structured to contact portions of the patient's face which tend to have a lower concentration of oil (as compared to the upper lip/mouth region).

Moreover, in the exemplary embodiment, adhesive layer 34 has a pull-off strength value throughout that is $\leq 40$ kPa ("pull-off strength limit value") to prevent damage to aged, sensitive and/or medically affected (e.g., diabetes, skin disease) skin. Also in the exemplary embodiment, adhesive layer 34 has a suggested adhesive shear strength value throughout (based on the analysis of scientific skin mechanics literature) that is $\leq 27$ kPa ("adhesive shear strength limit value") to prevent damage to aged, sensitive and/or medically affected (e.g., diabetes, skin disease) skin. In an alternative embodiment, adhesive layer 34 has a suggested adhesive shear strength value throughout (based on the analysis of scientific skin mechanics literature) that is $\leq 18$ kPa. Furthermore, in the exemplary embodiment, adhesive layer 34 has a suggested peel adhesion value of 0.15-0.2 N $mm^{-1}$ to avoid pain (it has been determined that beyond this limit is where persons experience pain from removal of adhesive materials).

Figure 2A:
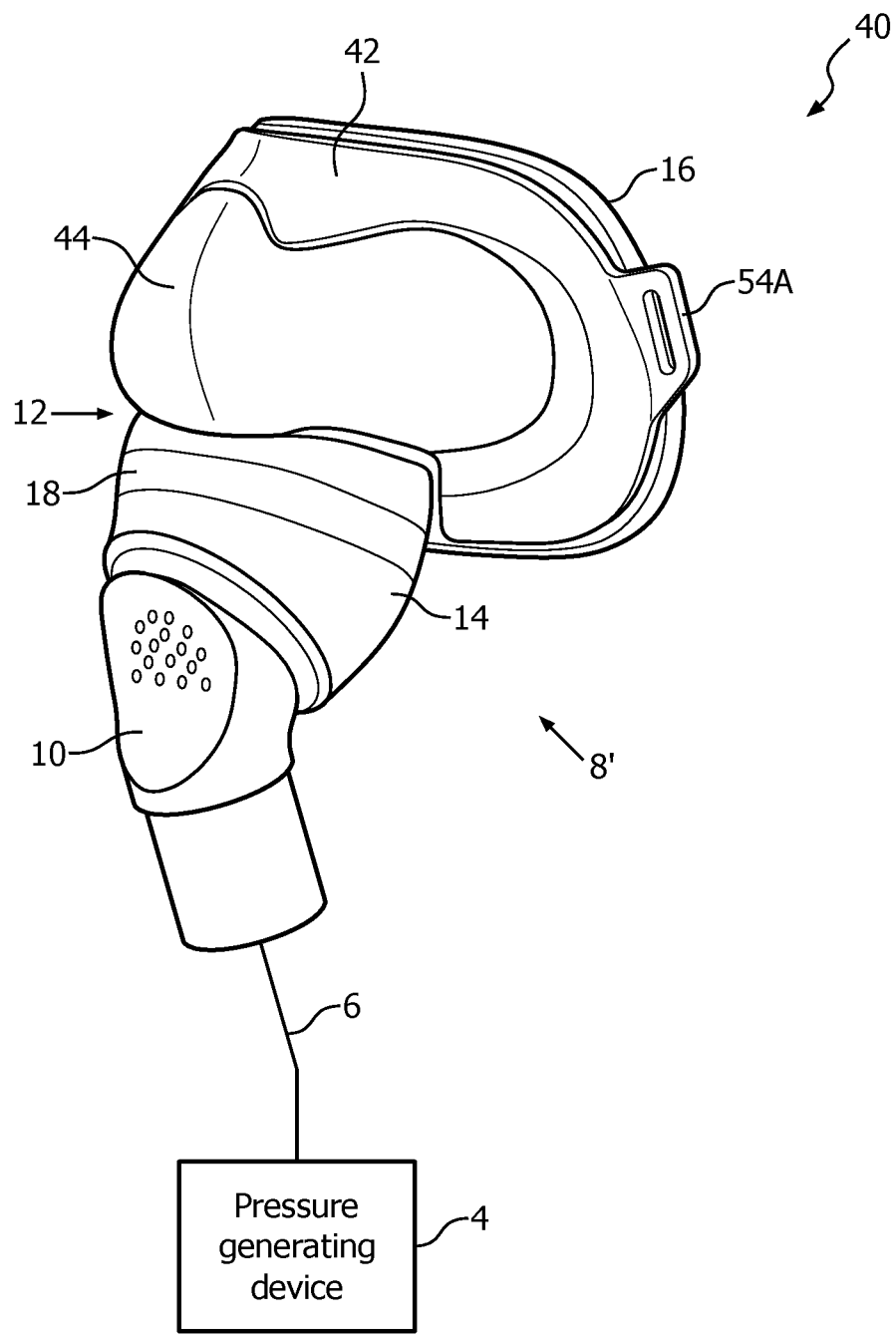
FIGS. 2A and 2B are schematic representations of a system adapted to provide a regimen of respiratory therapy to a patient according to an alternative exemplary embodiment.
Figure 2B:
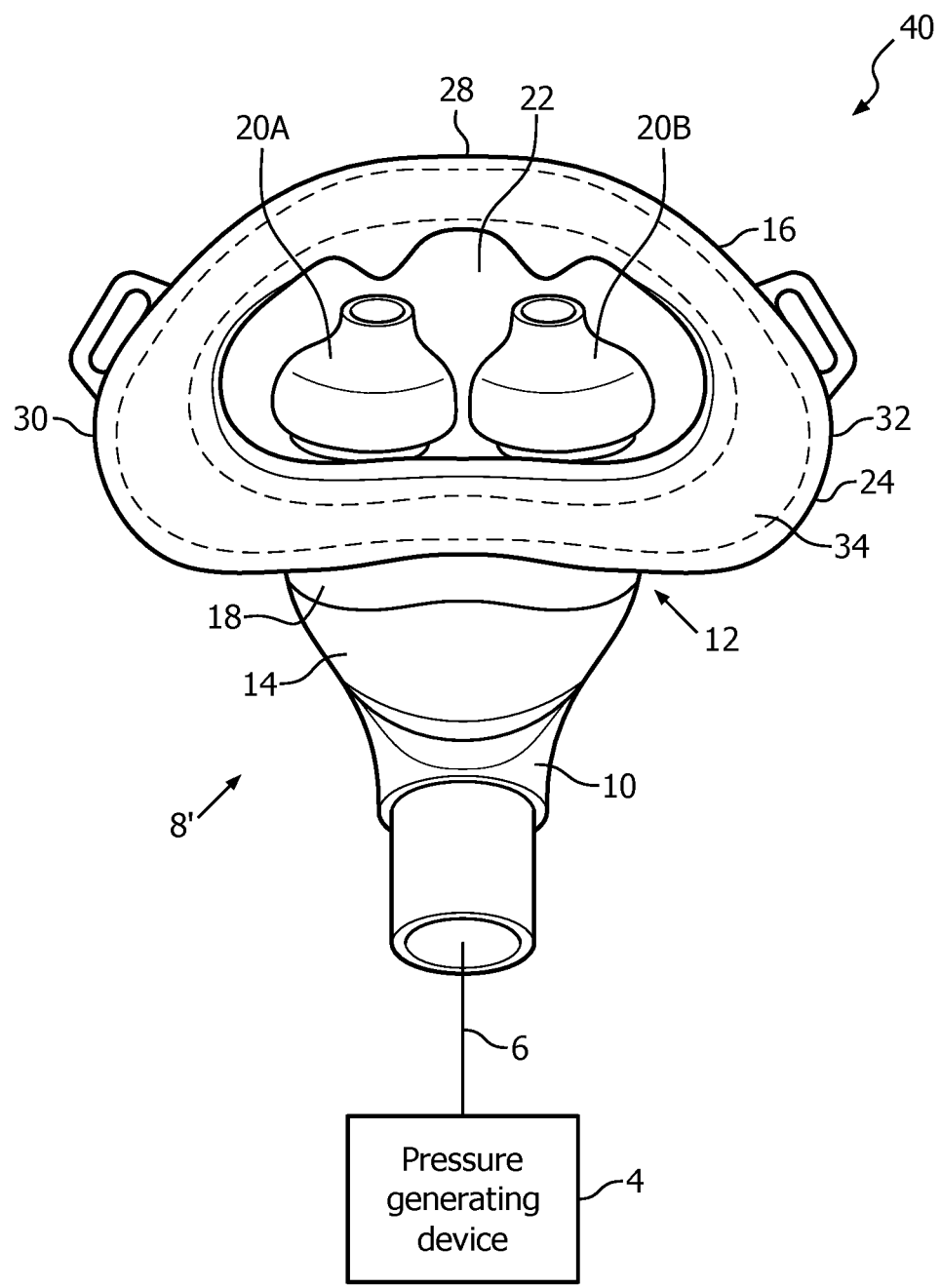

A system 40 adapted to provide a regimen of respiratory therapy to a patient according to another exemplary embodiment is generally shown in FIGS. 2A and 1B. System 40 includes many of the same components as system 2, and like components are labeled with like reference numerals. As seen FIGS. 2A and 2B, system 40 includes an alternative patient interface device 8'. Patient interface device 8' is similar to patient interface device 8 described above, and includes many of the same components, including nasal sealing cover 16 as described herein (which, in the exemplary embodiment, has the mechanical characteristics described above). However, as seen in FIG. 1A, patient interface device 8' further includes a nasal shell member 42 made of a rigid or semi-rigid material, such as, without limitation, an injection molded thermoplastic or silicone.

Figure 2C:
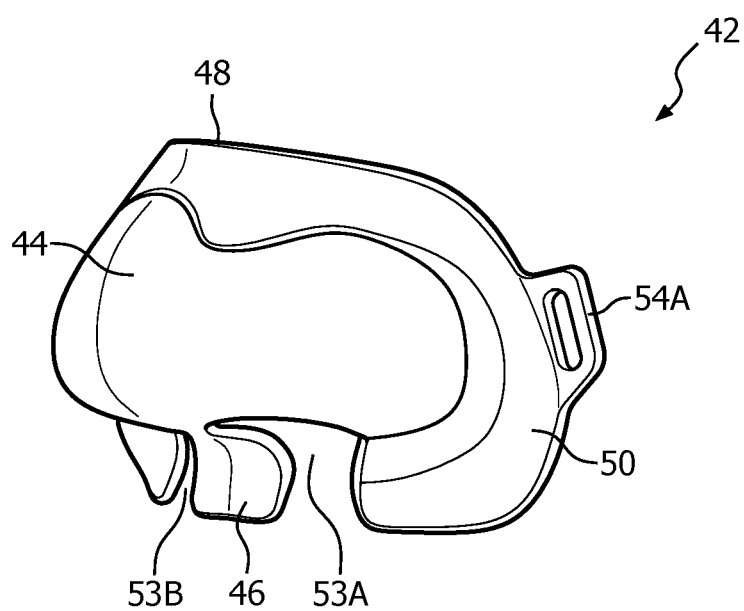
FIGS. 2C, 2D and 2E are isometric, front elevational and rear elevational views, respectively, of a nasal shell member forming a part of a patient interface device of the system of FIGS. 2A and 2B.
Figure 2D:
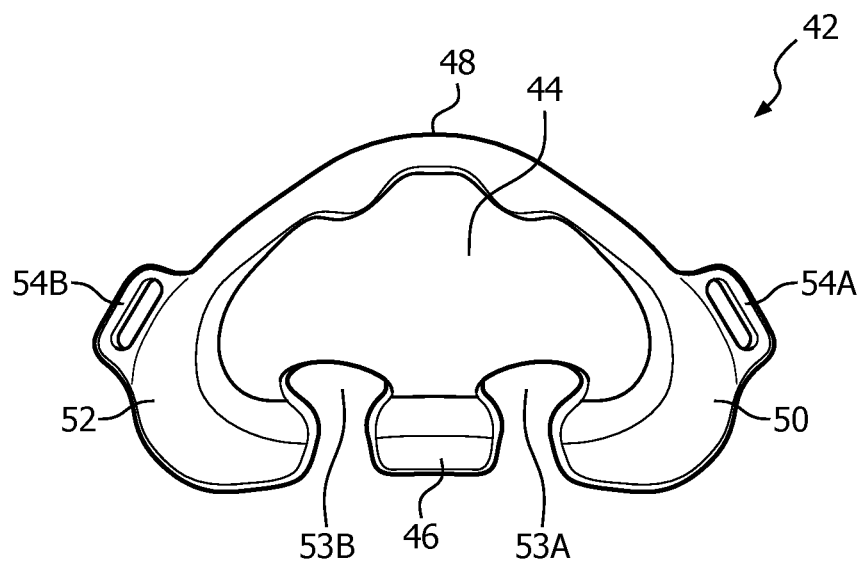
Figure 2E:
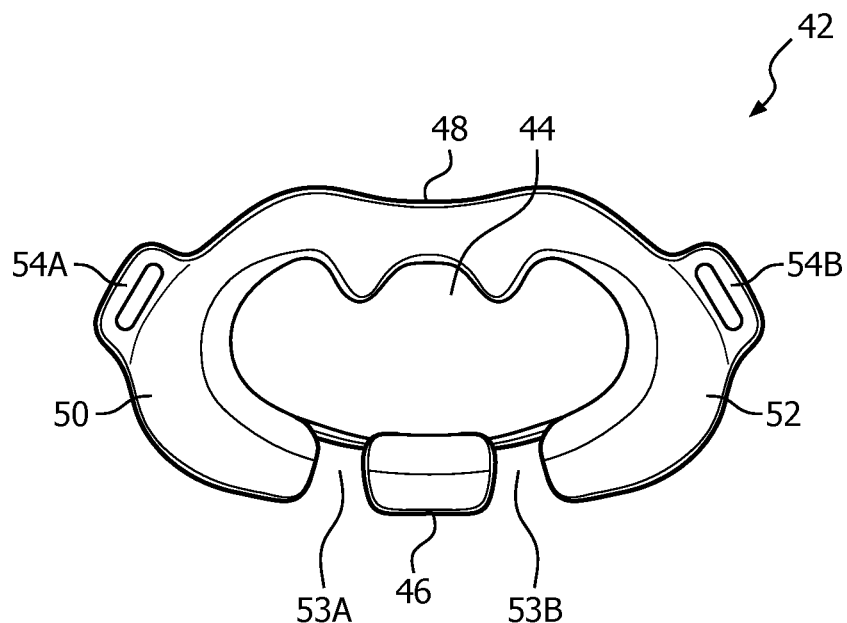

FIGS. 2C, 2D and 2E are isometric, front elevational and rear elevational views, respectively, of nasal shell member 42. Nasal shell member 42 is structured to match the shape of and overlay and receive therein nasal sealing cover 16. Thus, Nasal shell member 42 has a generally triangular shape including a central portion 44, a bottom/base region 46, an apex region 48 located opposite bottom region 46, a first side region 50 and a second side region 52 located opposite first side region 50. Bottom/base region 46 includes slots 53A and 53B for removeably receiving nasal prongs 20A and 20B. In addition, first side region 50 includes looped attachment member 54A and second side region 52 includes looped attachment member 54B. Looped attachment members 54A and 54B are structured to receive a strap member of a single strap headgear component (not shown) to provide additional stability and support for patient interface device 8'. In one embodiment, this additional stability and support also enables a lower shear strength adhesive to be used in adhesive layer 34, which may be beneficial for individuals with skin sensitivity and/or skin issues (diabetes, open woods, etc.).

Figure 3A:
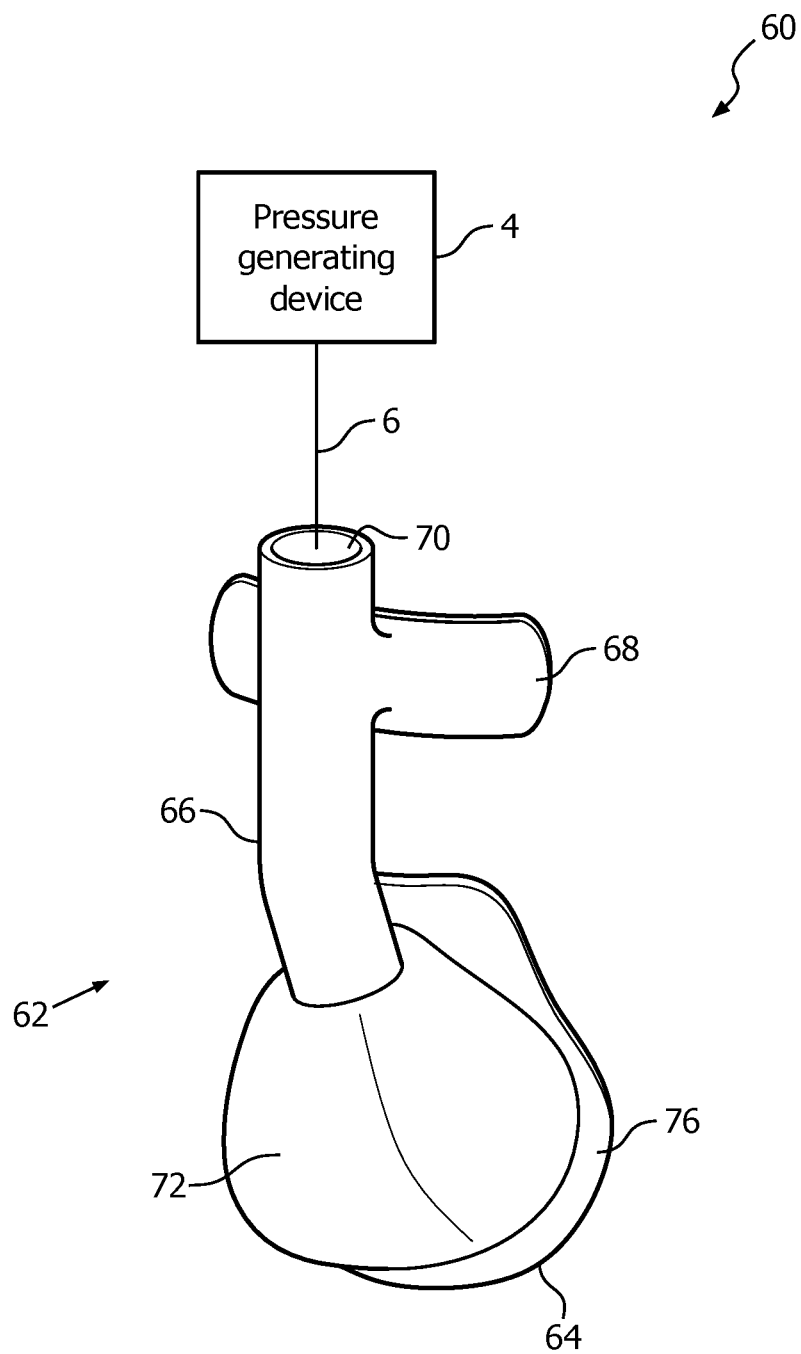
FIG. 3A is a schematic representation of a system adapted to provide a regimen of respiratory therapy to a patient according to a further alternative exemplary embodiment.

A system 60 adapted to provide a regimen of respiratory therapy to a patient according to another, alternative exemplary embodiment is generally shown in FIG. 3A. System 60 includes a pressure generating device 4 and a delivery conduit 6 (as described elsewhere herein) that are coupled to a patient interface device 62, described in detail below. Pressure generating device 4 is structured to generate a flow of breathing gas, and delivery conduit 6 is structured to communicate the flow of breathing gas from pressure generating device 4 to patient interface device 62. Delivery conduit 6 and patient interface device 62 are often collectively referred to as a patient circuit. As described below, in patient interface device 62, delivery conduit 6 connection is routed to the patient's forehead to decouple torque from delivery conduit 6 that might otherwise break the seal of patient interface device 62 with patient during sleep movement.

Figure 3B:
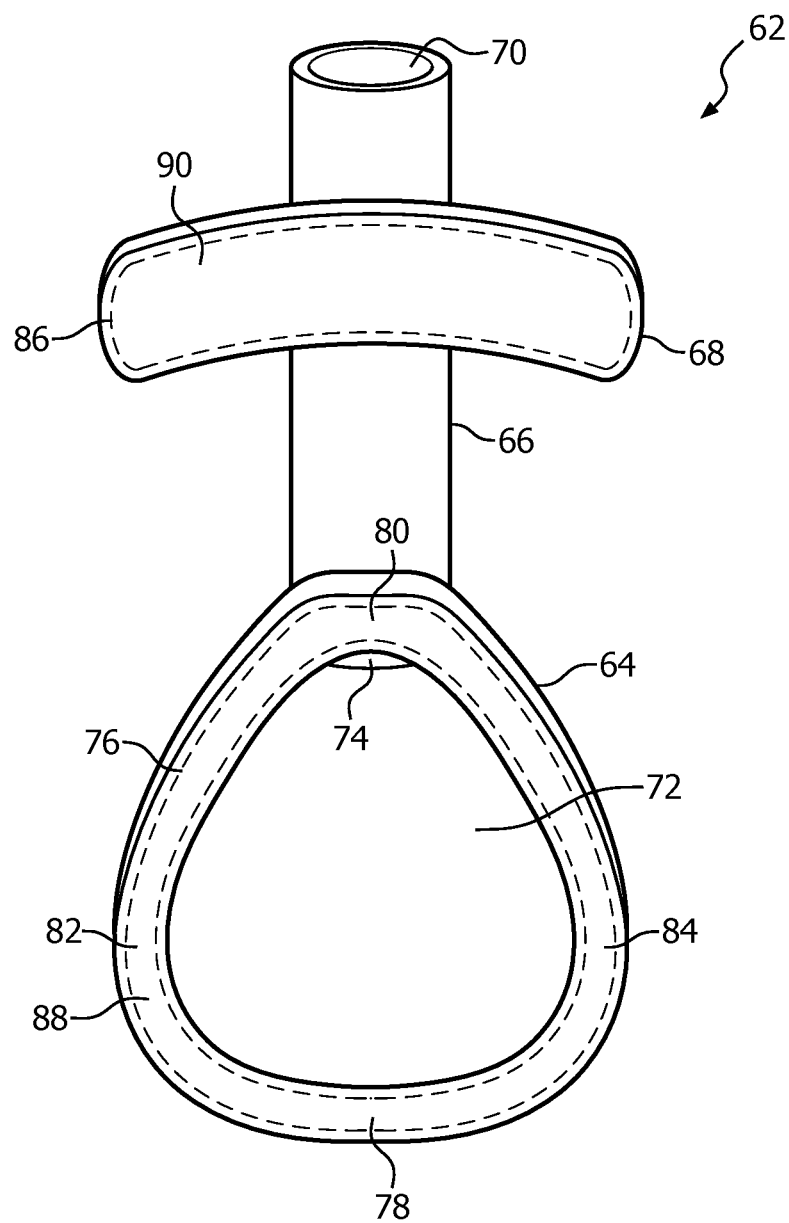
FIG. 3B is a rear elevational view of a patient interface device of the system of FIG. 3A.

FIG. 3B is a rear elevational view of patient interface device 62. As seen in FIGS. 3A and 3B, in the exemplary embodiment, patient interface device 62 is an integrated, unitary structure that is configured to deliver the flow of breathing gas generated by pressure generating device 4 to the airway of the patient. In one particular exemplary embodiment, patient interface device 62 is made of a flexible, cushiony, elastomeric material, such as, without limitation, silicone, an appropriately soft thermoplastic elastomer, a closed cell foam, or any combination of such materials. In another particular exemplary embodiment, patient interface device 62 is made of a rigid or semi-rigid material, such as, without limitation, an injection molded thermoplastic or silicone.

Patient interface device 62 includes a nasal mask portion 64 structured to sealingly cover the nose of a patient, a hollow delivery tube portion 66 fluidly connected to and extending from the top of nasal mask portion 64, and a forehead support portion 68 coupled to a distal end of delivery tube portion 66. The distal end of delivery tube portion 66 also includes a port portion 70 structured to enable delivery conduit 6 to be sealingly coupled to delivery tube portion 66 and thus patient interface device 62.

As noted above, nasal mask portion 64 is structured to surround and envelop the patient's nose when patient interface device 62 is donned by the patient, and includes a rounded central portion 72 for this purpose. Central portion 72 includes an aperture 74 for fluidly connecting nasal mask portion 64 to the proximal end of delivery tube portion 66. In addition, a contoured sealing edge portion 76 is coupled to and extends generally radially outwardly from the bottom of central portion 72. Sealing edge portion 76 is structured to sealingly engage the patient's face when patient interface device 62 is donned by the patient.

Referring to FIG. 3B, sealing edge portion 76 has a generally triangular shape including a bottom/base region 78, an apex region 80 located opposite bottom region 78, a first side region 82 and a second side region 84 located opposite first side region 82. Bottom/base region 78 is structured to sealingly engage the patient's upper lip/mouth region, apex region 80 is structured to sealingly engage the patient's nose bridge region (and includes a contoured indent for that purpose), and first side region 82 and second side region 84 are structured to sealingly engage the patient's cheek region. In addition, forehead support portion 68 includes a rear surface 86 structured to engage the patient's forehead when patient interface device 62 is donned by the patient.

Patient interface device 62 of the present embodiment is structured and configured to be secured to the patient's face without the need to also use a headgear apparatus coupled to patient interface device 62. In the exemplary embodiment, up to 50 g of patient interface device may be secured in this manner. Such securing of patient interface device 62 to the face is achieved by way of a first adhesive layer 88 (represented by the dotted lines in FIG. 3B, which could be continuous as shown or broken into a number of adjacent deposits) provided at/on certain portions of the inside surface of sealing edge portion 76, and a second adhesive layer 90 (also represented by the dotted lines in FIG. 3B, which could be continuous as shown or broken into a number of adjacent deposits). The securing of patient interface device 62 to the face in this manner relies, at least in part, on the shear force capabilities of the adhesive used in adhesive layers 88 and 90 across the area in which it is provided. The adhesive used in adhesive layers 88 and 90 is, in the exemplary embodiment, a medical-grade and/or biocompatible adhesive and may be, for example and without limitation, a silicone based adhesive or a polyurethane based adhesive. One suitable adhesive used in adhesive layers 88 and 90 is Silpuran® 2130, which is described elsewhere herein. In such an implementation, the application of Silpuran® 2130 may include no surface treatment, application of a primer, and/or application of a surface roughing to sealing edge portion 76 and rear surface 86 in the transverse direction relative to a peal pattern across the person's face (i.e., from left to right). Other suitable adhesives include, without limitation, Dow Corning® MG7-9900 and Technogel® BTGS-125AX.

In the exemplary embodiment, adhesive layers 88 and 90 have the particular characteristics and configurations described below (relating to adhesive shear strength, pull-off strength, layer thickness).

Furthermore, in an exemplary embodiment, adhesive layer 88 has the following mechanical characteristics. First, the adhesive used in adhesive layer 88 must react adhesively with human skin in a manner wherein it is able to be removeably bonded to the face while remaining cohesively bonded to the silicone or other material of patient interface device 62 (to mitigate the risk of adhesive material remaining on the patient's face, all adhesive material should decouple from the skin while remaining attached to patient interface device 62). Adhesive layer 88 has an area ($mm^2$) to adhesive shear strength (kPa) ratio of about 110 $mm^2$/kPa to about 200 $mm^2$/kPa, which range includes an area ($mm^2$) to adhesive shear strength (kPa) ratio of 115 determined by the present inventors to be optimal for dry skin and an area ($mm^2$) to adhesive shear strength (kPa) ratio of 196 determined by the present inventors to be optimal for oily skin. Adhesive layer 88 has an area ($mm^2$) to pull-off strength (kPa) ratio of about 45 $mm^2$/kPa to about 80 $mm^2$/kPa, which range includes an area ($mm^2$) to pull-off strength (kPa) ratio of 50.7 determined by the present inventors to be optimal for dry skin and an area (mm²) to pull-off strength (kPa) ratio of 76 determined by the present inventors to be optimal for oily skin.

Also, the thickness of adhesive layer 88 as deposited on the inside surface of sealing edge portion 76 ranges from 0.1 mm to 1.0 mm. In particular, in the exemplary embodiment, the thickness of adhesive layer 88 in bottom/base region 78 of sealing edge portion 76 is ≥0.1 mm and ≤0.5 mm (for optimal adhesive shear strength), because bottom/base region 76 is structured to contact the upper lip/mouth region of the patient, which tends to have a higher concentration of oil than other parts of the face. In addition, in the exemplary embodiment, the thickness of adhesive layer 88 in apex region 80, first side region 82, and second side region 84 of sealing edge portion 76 is ≥0.5 mm and ≤1.0 mm, because those regions are structured to contact portions of the patient's face which tend to have a lower concentration of oil (as compared to the upper lip/mouth region).

In addition, in the exemplary embodiment, adhesive layer 90 has the following mechanical characteristics. First, the adhesive used in adhesive layer 90 must react adhesively with human skin in a manner wherein it is able to be removeably bonded to the face while remaining cohesively bonded to the silicone or other material of patient interface device 62 (to mitigate the risk of adhesive material remaining on the patient's face, all adhesive material should decouple from the skin while remaining attached to patient interface device 62). Adhesive layer 90 has an area (mm²) to adhesive shear strength (kPa) ratio of about 100 mm²/kPa to about 185 mm²/kPa, which range includes an area (mm²) to adhesive shear strength (kPa) ratio of 105 determined by the present inventors to be optimal for dry skin and an area (mm²) to adhesive shear strength (kPa) ratio of 178.5 determined by the present inventors to be optimal for oily skin.

Adhesive layer 90 has an area (mm²) to pull-off strength (kPa) ratio of about 40 mm²/kPa to about 75 mm²/kPa, which range includes an area (mm²) to pull-off strength (kPa) ratio of 46 determined by the present inventors to be optimal for dry skin and an area (mm²) to pull-off strength (kPa) ratio of 69 determined by the present inventors to be optimal for oily skin. Also, the thickness of adhesive layer 90 as deposited on the rear surface 86 is ≥0.1 mm and ≤0.5 mm (for optimal adhesive shear strength), because rear surface 86 is structured to contact the forehead of the patient, which tends to have a higher concentration of oil than other parts of the face.

Moreover, in the exemplary embodiment, adhesive layers 88 and 90 both have a pull-off strength value throughout that is ≤40 kPa ("pull-off strength limit value") to prevent damage to aged, sensitive and/or medically affected (e.g., diabetes, skin disease) skin. Also in the exemplary embodiment, adhesive layers 88 and 90 each have a suggested adhesive shear strength value throughout (based on the analysis of scientific skin mechanics literature) that is ≤27 kPa ("adhesive shear strength limit value") to prevent damage to aged, sensitive and/or medically affected (e.g., diabetes, skin disease) skin. In an alternative embodiment, adhesive layers 88 and 90 each have a suggested adhesive shear strength value throughout (based on the analysis of scientific skin mechanics literature) that is ≤18 kPa. Furthermore, in the exemplary embodiment, adhesive layers 88 and 90 each have a suggested peel adhesion value of 0.15-0.2 N mm$^{-1}$ to avoid pain (it has been determined that beyond this limit is where persons experience pain from removal of adhesive materials).

In a further alternative embodiment, nasal mask portion 64 of patient interface device 62 could be replaced by a nasal pillows style mask having a structure similar to patient sealing assembly 12 described herein (FIGS. 1A-1F) including a nasal cushion 14 (fluidly coupled to delivery tube portion 66) and a nasal sealing cover 16 coupled to the nasal cushion 14, both as described elsewhere herein. Such an alternative patient interface device 62 would be structured and configured to be secured to the patient's face without the need to also use a headgear apparatus.

Figure 4A:
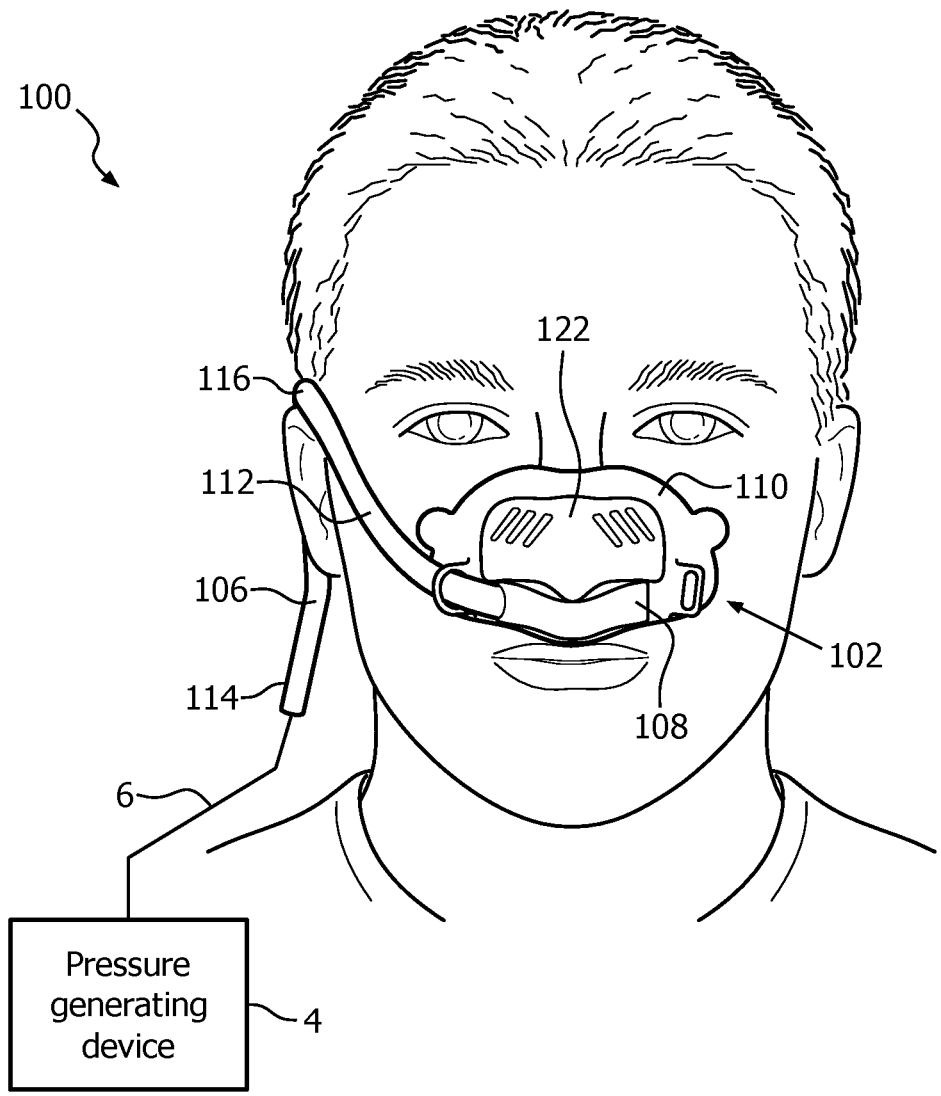
FIG. 4A is a schematic representation of a system adapted to provide a regimen of respiratory therapy to a patient according to a another alternative exemplary embodiment.

A system 100 adapted to provide a regimen of respiratory therapy to a patient according to still another, alternative exemplary embodiment is generally shown in FIG. 4A. System 100 includes a pressure generating device 4 and a delivery conduit 6 (as described elsewhere herein) that are coupled to a patient interface device 102, described in detail below. Pressure generating device 4 is structured to generate a flow of breathing gas, and delivery conduit 6 is structured to communicate the flow of breathing gas from pressure generating device 4 to patient interface device 102. Delivery conduit 6 and patient interface device 102 are often collectively referred to as a patient circuit.

Figure 4B:
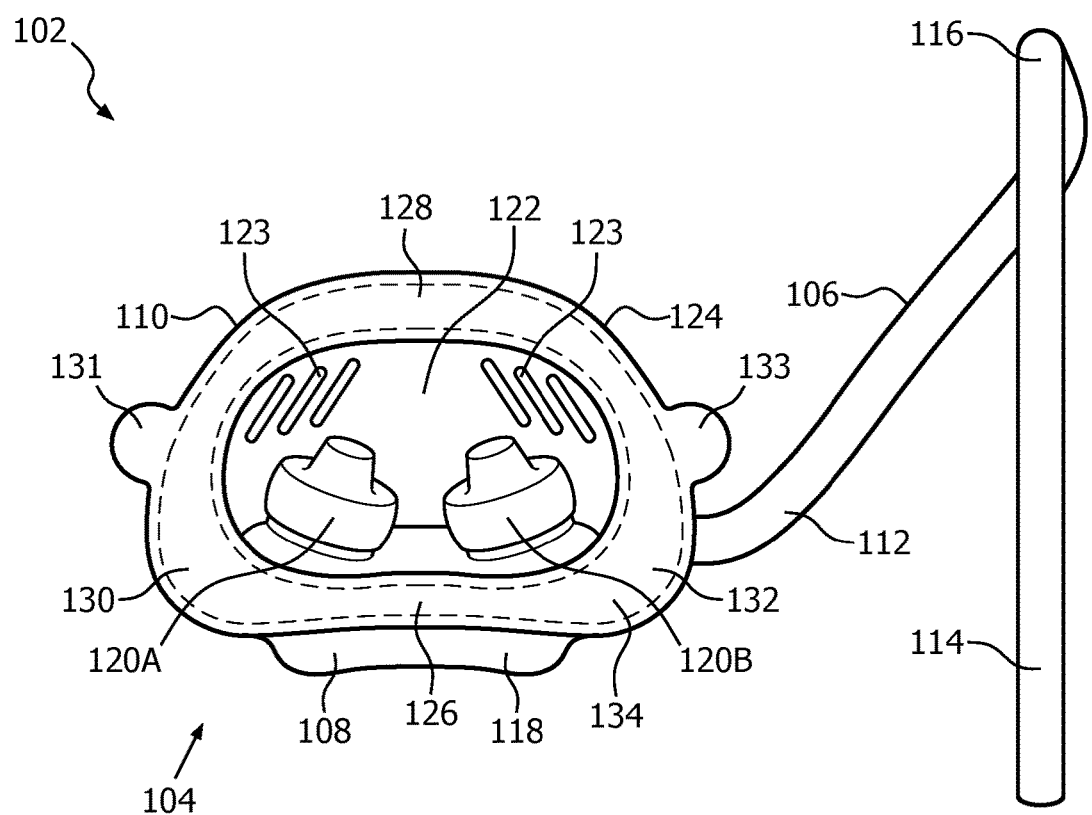
FIG. 4B is a rear elevational view of a patient interface device of the system of FIG. 4A.

FIG. 4B is a rear elevational view of patient interface device 102. Patient interface device 102 includes a patient sealing assembly 104 fluidly coupled to a hollow, U-shaped coupling/delivery conduit 106. Patient sealing assembly 104 facilitates the delivery of the flow of breathing gas to the airway of a patient, and includes a nasal cushion 108 and a nasal sealing cover 110 coupled to nasal cushion 108. Coupling/delivery conduit 106 includes a first portion 112 which is fluidly coupled to nasal cushion 108, a second portion 114 structured to be fluidly coupled to delivery conduit 6, and a U-shaped bend portion 116 provided between first portion 112 and second portion 114. As shown in FIG. 4A, U-shaped bend portion 116 is structured to fit over the patient's ear between the ear and the head in order to help secure patient interface device 102 to the head of the patient and help hold it in place.

In the illustrated embodiment, nasal cushion 108 is a "pillows" style nasal cushion made of a flexible, cushiony, elastomeric material, such as, without limitation, silicone, an appropriately soft thermoplastic elastomer, a closed cell foam, or any combination of such materials. As seen in FIG. 1B, the exemplary pillows style nasal cushion 108 includes a main body portion 118 having nasal prongs 120A and 120B. Nasal prongs 120A and 120B are structured to be received within the nares of the patient. Alternatively, nasal cushion 108 may be a "cradle" style nasal cushion that rests beneath and covers the patient's nares, or some other suitable nasal cushion configuration structured to engage the nose of the patient.

Nasal sealing cover 110 is structured to be removeably coupled to nasal cushion 108. Nasal sealing cover 110, like nasal cushion 108, is, in the exemplary embodiment, made of a flexible, cushiony, elastomeric material, such as, without limitation, silicone, an appropriately soft thermoplastic elastomer, a closed cell foam, or any combination of such materials. Nasal sealing cover 110 is also structured to surround and envelop nasal prongs 120A and 120B, and includes a central portion 122 having slots 123 for this purpose. A contoured sealing edge portion 124 is coupled to and extends generally radially outwardly from central portion 122. Sealing edge portion 124 is structured to sealingly engage the patient's face when patient interface device 102 is donned by the patient. Sealing edge portion 124 has a generally triangular shape including a bottom/base region 126, an apex region 128 located opposite bottom region 126, a first side region 130 and a second side region 132 located opposite first side region 130. Bottom/base region 126 is structured to sealingly engage the patient's upper lip/mouth region, apex region 128 is structured to sealingly engage the patient's nose bridge region (and includes a contoured indent for that purpose), and first side region 130 and second side region 132 are structured to sealingly engage the patient's cheek region.

Patient interface device 102 of the present embodiment is structured and configured to be secured to the patient's face without the need to also use a headgear apparatus coupled to patient interface device 102. In the exemplary embodiment, up to 50 g of patient interface device may be secured in this manner. Such securing of patient interface device 102 to the face is achieved by way of an adhesive layer 134 (represented by the dotted lines in FIG. 4B, which could be continuous as shown or broken into a number of adjacent deposits) provided at/on certain portions of the inside surface of sealing edge portion 126. The securing of patient interface device 102 to the face in this manner relies, at least in part, on the shear force capabilities of the adhesive used in adhesive layer 134 across the area in which it is provided. Facial removal tab 131 is provided on first side region 130 and facial removal tab 133 is provided on second side region 132. Facial removal tabs 131 and 133 encourage pulling, mitigating the sheer component at mask removal.

The adhesive used in adhesive layer 134 is, in the exemplary embodiment, a medical-grade and/or biocompatible adhesive and may be, for example and without limitation, a silicone based adhesive or a polyurethane based adhesive. One suitable adhesive used in adhesive layer 134 is Silpuran® 2130, which is described elsewhere herein. In such an implementation, the application of Silpuran® 2130 may include no surface treatment, application of a primer, and/or application of a surface roughing to sealing edge portion 124 in the transverse direction relative to a peal pattern across the person's face (i.e., from left to right). Other suitable adhesives include, without limitation, Dow Corning® MG7-9900 and Technogel® BTGS-125AX.

In the exemplary embodiment, adhesive layer 134 has the particular characteristics and configurations described below (relating to adhesive shear strength, pull-off strength, layer thickness).

Furthermore, in an exemplary embodiment, adhesive layer 134 has the following mechanical characteristics. First, the adhesive used in adhesive layer 134 must react adhesively with human skin in a manner wherein it is able to be removeably bonded to the face while remaining cohesively bonded to the silicone or other material of nasal sealing cover 110 (to mitigate the risk of adhesive material remaining on the patient's face, all adhesive material should decouple from the skin while remaining attached to nasal sealing cover 110). Adhesive layer 134 has an area ($mm^2$) to adhesive shear strength (kPa) ratio of about 140 $mm^2$/kPa to about 270 $mm^2$/kPa, which range includes an area ($mm^2$) to adhesive shear strength (kPa) ratio of 150 determined by the present inventors to be optimal for dry skin and an area ($mm^2$) to adhesive shear strength (kPa) ratio of 257 determined by the present inventors to be optimal for oily skin.

Adhesive layer 134 has an area ($mm^2$) to pull-off strength (kPa) ratio of about 60 $mm^2$/kPa to about 105 $mm^2$/kPa, which range includes an area ($mm^2$) to pull-off strength (kPa) ratio of 66.3 determined by the present inventors to be optimal for dry skin and an area ($mm^2$) to pull-off strength (kPa) ratio of 99.5 determined by the present inventors to be optimal for oily skin. Also, the thickness of adhesive layer 134 as deposited on the inside surface of sealing edge portion 124 ranges from 0.1 mm to 1.0 mm. In particular, in the exemplary embodiment, the thickness of adhesive layer 134 in bottom/base region 126 of sealing edge portion 124 is ≥0.1 mm and ≤0.5 mm (for optimal adhesive shear strength), because bottom/base region 126 is structured to contact the upper lip/mouth region of the patient, which tends to have a higher concentration of oil than other parts of the face. In addition, in the exemplary embodiment, the thickness of adhesive layer 134 in apex region 128, first side region 130, and second side region 132 of sealing edge portion 124 is ≥0.5 mm and ≤1.0 mm, because those regions are structured to contact portions of the patient's face which tend to have a lower concentration of oil (as compared to the upper lip/mouth region).

Moreover, in the exemplary embodiment, adhesive layer 134 has a pull-off strength value throughout that is ≤40 kPa ("pull-off strength limit value") to prevent damage to aged, sensitive and/or medically affected (e.g., diabetes, skin disease) skin. Also in the exemplary embodiment, adhesive layer 134 has a suggested adhesive shear strength value throughout (based on the analysis of scientific skin mechanics literature) that is ≤27 kPa ("adhesive shear strength limit value") to prevent damage to aged, sensitive and/or medically affected (e.g., diabetes, skin disease) skin. In an alternative embodiment, adhesive layer 134 has a suggested adhesive shear strength value throughout (based on the analysis of scientific skin mechanics literature) that is ≤18 kPa. Furthermore, in the exemplary embodiment, adhesive layer 134 has a suggested peel adhesion value of 0.15-0.2 N $mm^{-1}$ to avoid pain (it has been determined that beyond this limit is where persons experience pain from removal of adhesive materials).

Figure 5A:
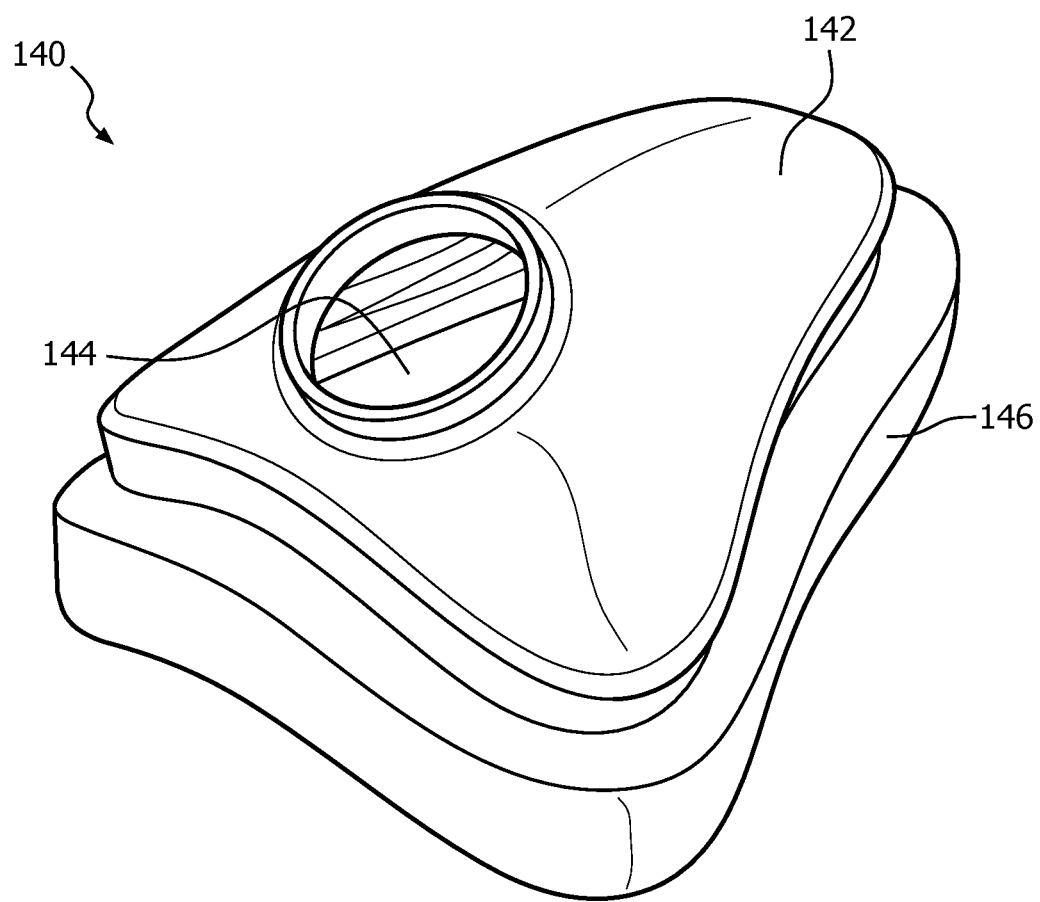
FIG. 5A is an isometric view and FIG. 5B is a rear elevational view of a mask according to a further alternative embodiment of the invention.
Figure 5B:
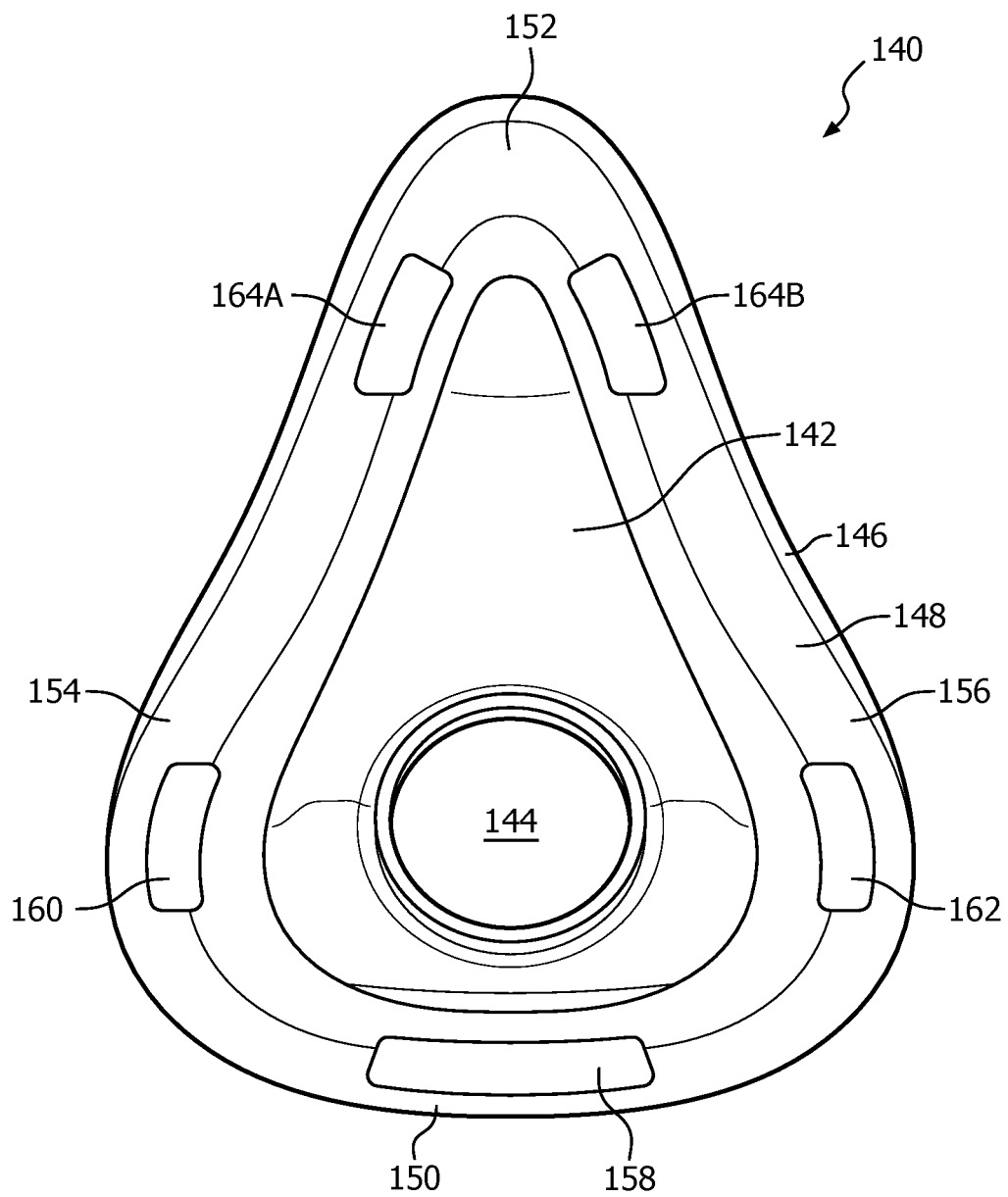

FIG. 5A is an isometric view and FIG. 5B is a rear elevational view of a mask 140 according to a further alternative embodiment of the invention. In the illustrated embodiment, mask 140 is a full face mask type mask, but it will be understood that mask 140 may also be a nasal mask. Mask 140 includes faceplate 142 having a hole 144 structured for fluid connection to a fluid coupling device such as an elbow conduit. In the exemplary embodiment, faceplate 142 made of a rigid or semi-rigid material, such as, without limitation, an injection molded thermoplastic or silicone. Mask 140 further includes a cushion 146 coupled to faceplate 142. Cushion 146 is structured to sealingly engage the patient's face and is made of a flexible, cushiony, elastomeric material, such as, without limitation, silicone, an appropriately soft thermoplastic elastomer, a closed cell foam, or any combination of such materials.

Cushion 146 has a generally triangular shape, and includes a sealing surface 148 including a bottom/base region 150, an apex region 152 located opposite bottom region 150, a first side region 154 and a second side region 156 located opposite first side region 154. Bottom/base region 150 is structured to sealingly engage the patient's lower lip/mouth region, apex region 152 is structured to sealingly engage the patient's nose bridge region, and first side region 154 and second side region 156 are structured to sealingly engage the patient's cheek region.

In order facilitate securing of mask 140 to the patient's face using, for example, a suitable headgear, adhesive layers 158, 160, 162, 164A and 164B are provided at/on certain portions of the sealing surface 148. The adhesive used in adhesive layers 158, 160, 162, 164A and 164B may be, for example and without limitation, a silicone based adhesive or a polyurethane based adhesive. In the exemplary, adhesive layers 158, 160, 162, 164A and 164B are provided in select areas where leakage is present and which therefore normally necessitates more strapping force to overcome such leakage. In particular, adhesive layer 158 is provided on bottom/base region 150, adhesive layer 160 is provided on first side region 154, adhesive layer 162 is provided on second side region 156, and adhesive layers 164A and 164B are provided on opposite sides of apex region 152.

In the exemplary embodiment, the adhesive and adhesive layers 158, 160, 162, 164A and 164B have the particular characteristics and configurations described below (relating to adhesive shear strength, pull-off strength, layer thickness).

Furthermore, in an exemplary embodiment, adhesive layer 158 has an area ($mm^2$) to adhesive shear strength (kPa) ratio of about 10 $mm^2$/kPa to about 25 $mm^2$/kPa, which range includes an area ($mm^2$) to adhesive shear strength (kPa) ratio of 14 determined by the present inventors to be optimal for dry skin and an area ($mm^2$) to adhesive shear strength (kPa) ratio of 23 determined by the present inventors to be optimal for oily skin. Adhesive layer 158 has an area ($mm^2$) to pull-off strength (kPa) ratio of about 4 $mm^2$/kPa to about 12 $mm^2$/kPa, which range includes an area ($mm^2$) to pull-off strength (kPa) ratio of 6.16 determined by the present inventors to be optimal for dry skin and an area ($mm^2$) to pull-off strength (kPa) ratio of 9.2 determined by the present inventors to be optimal for oily skin. Also, the thickness of adhesive layer 158 is ≥0.1 mm and ≤0.5 mm (for optimal adhesive shear strength), because bottom/base region 150 is structured to contact the lower lip/mouth/chin region of the patient, which tends to have a higher concentration of oil than other parts of the face.

Also in the exemplary embodiment, adhesive layers 160 and 162 each have an area ($mm^2$) to adhesive shear strength (kPa) ratio of about 5 $mm^2$/kPa to about 15 $mm^2$/kPa, which range includes an area ($mm^2$) to adhesive shear strength (kPa) ratio of 7.4 determined by the present inventors to be optimal for dry skin and an area ($mm^2$) to adhesive shear strength (kPa) ratio of 13.2 determined by the present inventors to be optimal for oily skin. Adhesive layers 160 and 162 each have an area ($mm^2$) to pull-off strength (kPa) ratio of about 2 $mm^2$/kPa to about 7 $mm^2$/kPa, which range includes an area ($mm^2$) to pull-off strength (kPa) ratio of 3.4 determined by the present inventors to be optimal for dry skin and an area ($mm^2$) to pull-off strength (kPa) ratio of 5.14 determined by the present inventors to be optimal for oily skin. Also, the thickness of each of adhesive layers 160 and 162 is ≥0.5 mm and ≤1.0 mm (for optimal adhesive shear strength), because first side region 154, and second side region 156 are structured to contact portions of the patient's face (cheek) which tend to have a lower concentration of oil (as compared to the lower lip/mouth/chin region).

In addition, in the exemplary embodiment, adhesive layers 164A and 164B each have an area ($mm^2$) to adhesive shear strength (kPa) ratio of about 5 $mm^2$/kPa to about 13 $mm^2$/kPa, which range includes an area ($mm^2$) to adhesive shear strength (kPa) ratio of 6.83 determined by the present inventors to be optimal for dry skin and an area ($mm^2$) to adhesive shear strength (kPa) ratio of 11.5 determined by the present inventors to be optimal for oily skin. Adhesive layers 164A and 164B each have an area ($mm^2$) to pull-off strength (kPa) ratio of about 2 $mm^2$/kPa to about 6 $mm^2$/kPa, which range includes an area ($mm^2$) to pull-off strength (kPa) ratio of 3 determined by the present inventors to be optimal for dry skin and an area ($mm^2$) to pull-off strength (kPa) ratio of 4.5 determined by the present inventors to be optimal for oily skin. Also, the thickness of each of adhesive layers 164A and 164B is ≥0.5 mm and ≤1.0 mm (for optimal adhesive shear strength), because apex region 152 is structured to contact portions of the patient's face (cheek) which tend to have a lower concentration of oil (as compared to the lower lip/mouth/chin region).

Moreover, in the exemplary embodiment, adhesive layers 158, 160, 162, 164A and 164B each has a pull-off strength value throughout that is ≤40 kPa ("pull-off strength limit value") to prevent damage to aged, sensitive and/or medically affected (e.g., diabetes, skin disease) skin. Also in the exemplary embodiment, adhesive layers 158, 160, 162, 164A and 164B each has a suggested adhesive shear strength value throughout (based on the analysis of scientific skin mechanics literature) that is ≤27 kPa ("adhesive shear strength limit value") to prevent damage to aged, sensitive and/or medically affected (e.g., diabetes, skin disease) skin. In an alternative embodiment, adhesive layers 158, 160, 162, 164A and 164B each has a suggested adhesive shear strength value throughout (based on the analysis of scientific skin mechanics literature) that is ≤18 kPa. Furthermore, in the exemplary embodiment, adhesive layers 158, 160, 162, 164A and 164B each have a suggested peel adhesion value of 0.15-0.2 N $mm^{-1}$ to avoid pain (it has been determined that beyond this limit is where persons experience pain from removal of adhesive materials).

Figure 5C:
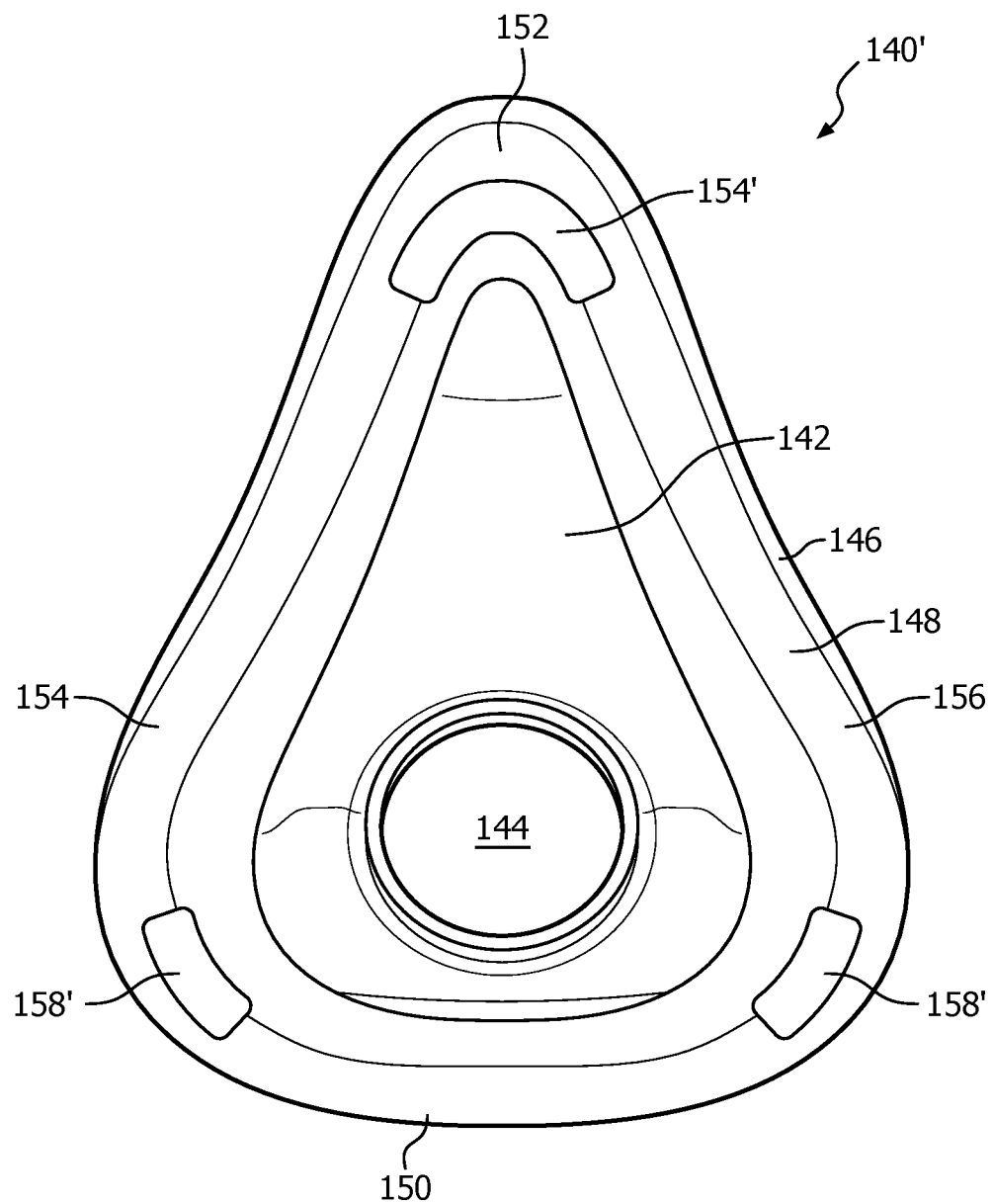
FIG. 5C is a rear elevational view of a mask according to another alternative embodiment of the invention.

FIG. 5C is a rear elevational view of a mask 140' according to another alternative embodiment of the invention. Mask 140' is similar to mask 140, and like parts are labeled with like reference numerals. In addition, in order facilitate securing of mask 140' to the patient's face using, for example, a suitable headgear, adhesive layers 158', and 164' are provided at/on certain portions of the sealing surface 148. The positioning of the adhesive layers in mask 140' has been determined by the present inventors to be particularly well suited for facial features and/or structures that are common to individuals of Caucasian descent/ancestry. In particular, adhesive layers 158' are provided on opposite sides of bottom/base region 150 at points that are immediately adjacent to first side region 154 and second side region 156, respectively, and adhesive layer 164' is provided on apex region 152 spanning from one side to the other of apex region 152 through the middle of apex region 152. In the exemplary embodiment, the adhesive and adhesive layers 158' and 164' have the particular characteristics and configurations described above in connection with mask 140 (relating to adhesive shear strength, pull-off strength, layer thickness). In particular, adhesive layers 158' each have an area ($mm^2$) to pull-off strength (kPa) ratio of about 4 $mm^2$/kPa to about 12 $mm^2$/kPa, which range includes an area ($mm^2$) to pull-off strength (kPa) ratio of 6.16 determined by the present inventors to be optimal for dry skin and an area ($mm^2$) to pull-off strength (kPa) ratio of 9.2 determined by the present inventors to be optimal for oily skin.

Also, the thickness of each of adhesive layers 158' is ≥0.1 mm and ≤0.5 mm (for optimal adhesive shear strength), because bottom/base region 150 is structured to contact the lower lip/mouth/chin region of the patient, which tends to have a higher concentration of oil than other parts of the face. Adhesive layer 164' has an area ($mm^2$) to pull-off strength (kPa) ratio of about 2 $mm^2$/kPa to about 6 $mm^2$/kPa, which range includes an area ($mm^2$) to pull-off strength (kPa) ratio of 3 determined by the present inventors to be optimal for dry skin and an area ($mm^2$) to pull-off strength (kPa) ratio of 4.5 determined by the present inventors to be optimal for oily skin. Also, the thickness of adhesive layer 164' is ≥0.5 mm and ≤1.0 mm (for optimal adhesive shear strength), because apex region 152 is structured to contact portions of the patient's face (cheek) which tend to have a lower concentration of oil (as compared to the lower lip/mouth/chin region).

Figure 5D:
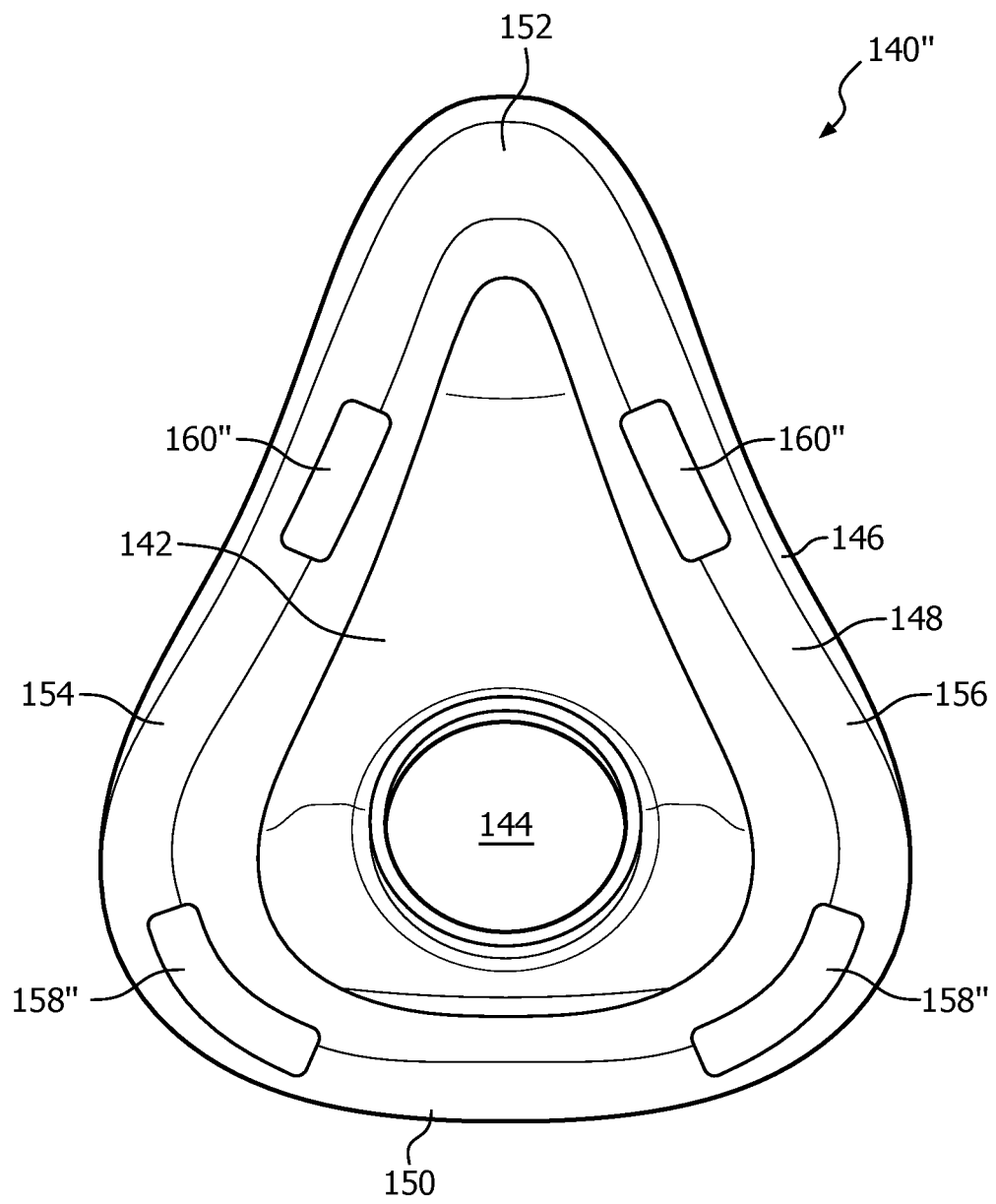
FIG. 5D is a rear elevational view of a mask according to yet another alternative embodiment of the invention.

FIG. 5D is a rear elevational view of a mask 140" according to yet another alternative embodiment of the invention. Mask 140" is similar to mask 140, and like parts are labeled with like reference numerals. In addition, in order facilitate securing of mask 140" to the patient's face using, for example, a suitable headgear, adhesive layers 158", and 160" are provided at/on certain portions of the sealing surface 148. The positioning of the adhesive layers in mask 140" has been determined by the present inventors to be particularly well suited for facial features and/or structures that are common to individuals of Asian descent/ancestry. In particular, adhesive layers 158" are provided on opposite sides of bottom/base region 150 at points that are immediately adjacent to first side region 154 and second side region 156, respectively, and adhesive layer 160" are provided on first side region 154 and second side region 156, respectively, immediately adjacent to apex region 152. In the exemplary embodiment, the adhesive and adhesive layers 158" and 160" have the particular characteristics and configurations described above in connection with mask 140 (relating to adhesive shear strength, pull-off strength, layer thickness). In particular, adhesive layers 158" each have an area (mm$^2$) to pull-off strength (kPa) ratio of about 4 mm$^2$/kPa to about 12 mm$^2$/kPa, which range includes an area (mm$^2$) to pull-off strength (kPa) ratio of 6.16 determined by the present inventors to be optimal for dry skin and an area (mm$^2$) to pull-off strength (kPa) ratio of 9.2 determined by the present inventors to be optimal for oily skin.

Also, the thickness of each of adhesive layers 158" is ≥0.1 mm and ≤0.5 mm (for optimal adhesive shear strength), because bottom/base region 150 is structured to contact the lower lip/mouth/chin region of the patient, which tends to have a higher concentration of oil than other parts of the face. Adhesive layers 160" each have an area (mm$^2$) to adhesive shear strength (kPa) ratio of about 5 mm$^2$/kPa to about 15 mm$^2$/kPa, which range includes an area (mm$^2$) to adhesive shear strength (kPa) ratio of 7.4 determined by the present inventors to be optimal for dry skin and an area (mm$^2$) to adhesive shear strength (kPa) ratio of 13.2 determined by the present inventors to be optimal for oily skin. Adhesive layers 160" each have an area (mm$^2$) to pull-off strength (kPa) ratio of about 2 mm$^2$/kPa to about 7 mm$^2$/kPa, which range includes an area (mm$^2$) to pull-off strength (kPa) ratio of 3.4 determined by the present inventors to be optimal for dry skin and an area (mm$^2$) to pull-off strength (kPa) ratio of 5.14 determined by the present inventors to be optimal for oily skin. Also, the thickness of each of adhesive layers 160" is ≥0.5 mm and ≤1.0 mm (for optimal adhesive shear strength), because first side region 154, and second side region 156 are structured to contact portions of the patient's face (cheek) which tend to have a lower concentration of oil (as compared to the lower lip/mouth/chin region).

Figure 6A:
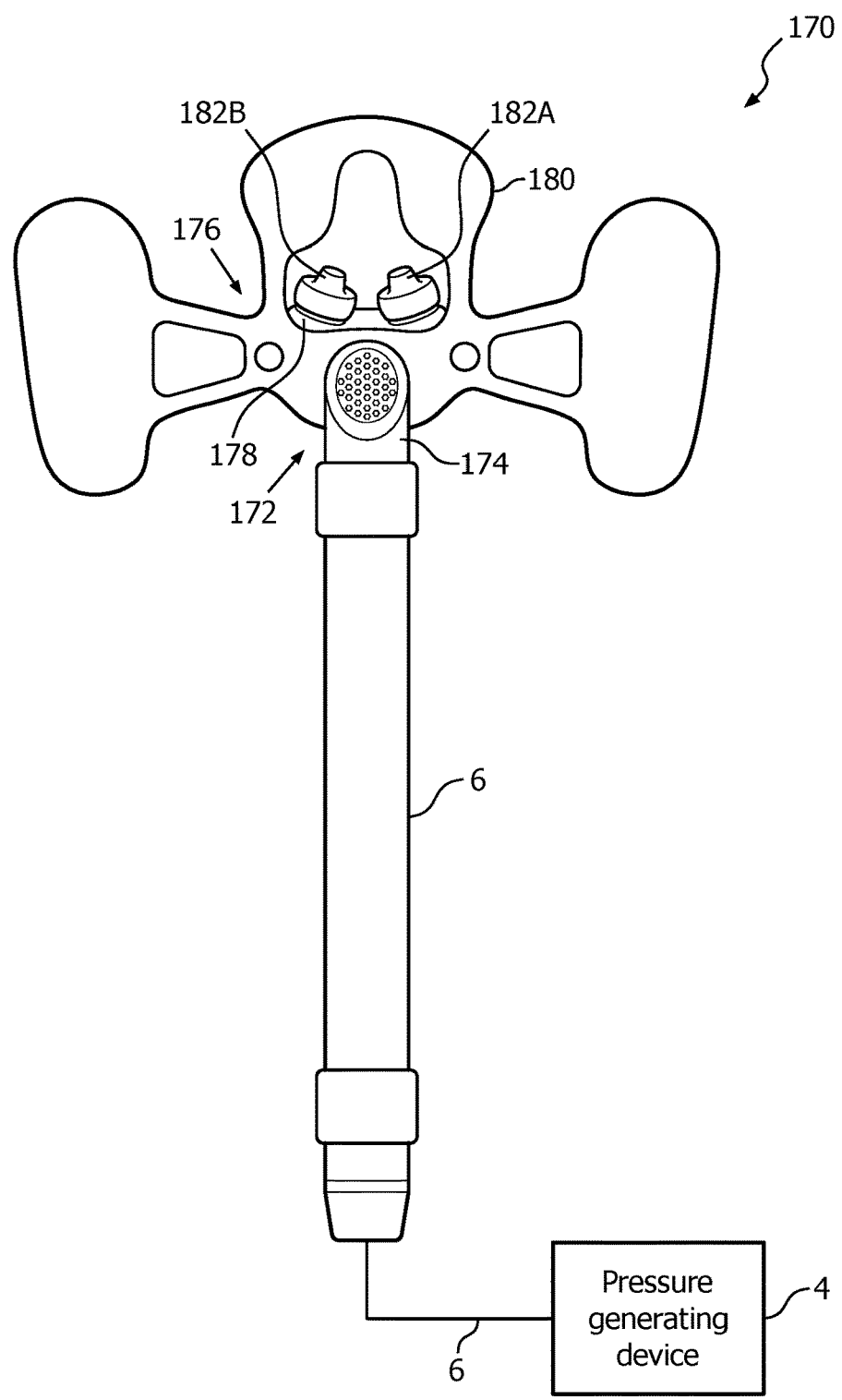
FIG. 6A is a schematic representation of a system adapted to provide a regimen of respiratory therapy to a patient according to another alternative exemplary embodiment.

A system 170 adapted to provide a regimen of respiratory therapy to a patient according to a further alternative exemplary embodiment is generally shown in FIG. 6A. System 170 includes a pressure generating device 4 and a delivery conduit 6 (as described elsewhere herein) that are coupled to a patient interface device 172, described in detail below. Pressure generating device 4 is structured to generate a flow of breathing gas, and delivery conduit 6 is structured to communicate the flow of breathing gas from pressure generating device 4 to patient interface device 62. Delivery conduit 6 and patient interface device 172 are often collectively referred to as a patient circuit.

As seen in FIG. 6A, patient interface device 172 includes an elbow conduit 174 that is coupled to a patient sealing assembly 176. Patient sealing assembly 176 facilitates the delivery of the flow of breathing gas to the airway of a patient. Patient sealing assembly 176 includes a nasal cushion 178 and an attachment pad 180 coupled to nasal cushion 178.

In the illustrated embodiment, nasal cushion 178 is a "pillows" style nasal cushion made of a flexible, cushiony, elastomeric material, such as, without limitation, silicone, an appropriately soft thermoplastic elastomer, a closed cell foam, or any combination of such materials. The exemplary pillows style nasal cushion 178 includes a main body portion having nasal prongs 182A and 182B extending from a top side thereof. Nasal prongs 182A and 182B are structured to be received within the nares of the patient. Alternatively, nasal cushion 178 may be a "cradle" style nasal cushion that rests beneath and covers the patient's nares, or some other suitable nasal cushion configuration structured to engage the nose of the patient.

Patient interface device 172 of the present embodiment is structured and configured to be secured to the patient's face without the need to also use a headgear apparatus coupled to patient interface device 172. In the exemplary embodiment, up to 50 g of patient interface device may be secured in this manner. Such securing of patient interface device 172 to the face is achieved by way of a number of adhesive layers (described below) provided at/on certain portions of the inside surface of attachment pad 180, and relies, at least in part, on the shear force capabilities of the adhesive used in the adhesive layers across the areas in which they are provided. The adhesive used in the adhesive layers described below may be, for example and without limitation, a silicone based adhesive or a polyurethane based adhesive.

Figure 6B:
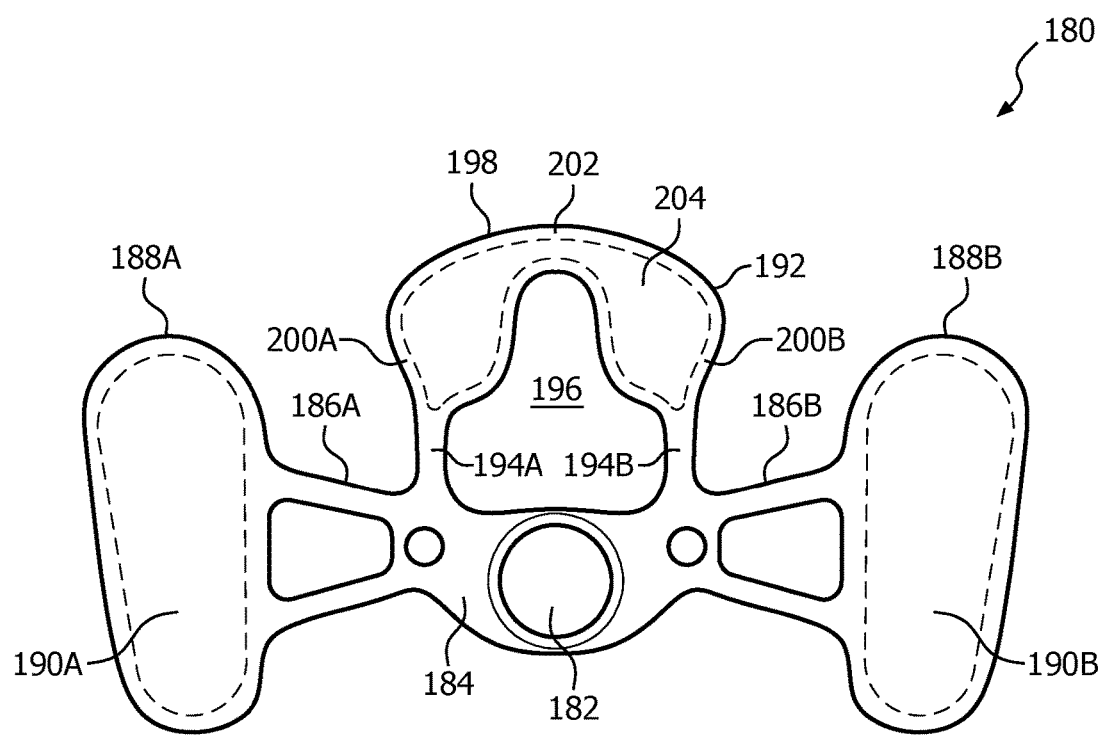
FIG. 6B is a rear elevational view of an attachment pad forming part of the patient interface device of the system of FIG. 6A.

FIG. 6B is a rear isometric view of attachment pad 180. Attachment pad 180 is structured to be removeably coupled to nasal cushion 178 and elbow conduit 174 by inserting a portion of elbow conduit 174 through a central orifice 182 provided in a central body 184 of attachment pad 180 so that it may engage and couple to nasal cushion 178 as shown in FIG. 6A. Attachment pad 180, like nasal cushion 178, is, in the exemplary embodiment, made of a flexible, cushiony, elastomeric material, such as, without limitation, silicone, an appropriately soft thermoplastic elastomer, a closed cell foam, or any combination of such materials.

Referring to FIG. 6B, attachment pad 180 further includes a first arm member 186A extending from a first side of central body 184 and a second arm member 186B extending from a second side of central body 184. First arm member 186A includes an oblong cheek attachment portion 188A at a distal end thereof, and similarly second arm member 186B includes an oblong cheek attachment portion 188B at a distal end thereof. As seen FIG. 6B, cheek attachment portion 188A includes an adhesive layer 190A on the rear side thereof, and cheek attachment portion 188B includes an adhesive layer 190B on the rear side thereof.

Attachment pad 180 also further includes a nasal attachment member 192 that extends from a top portion of central body 184 by way of legs 194A and 194B and that together with central body 184 define a nasal orifice 196. Nasal attachment member 192 further includes a nose bridge portion 198 that comprises a first enlarged member 200A, a second enlarged member 200B, and a narrow connecting member 202 provided in between first enlarged member 200A and second enlarged member 200B (first enlarged member 200A and second enlarged member 200B extend downwardly from connecting member 202 to define an arced portion of nasal orifice 196 for receiving the bridge of the patient's nose). Nose bridge portion 198 includes an adhesive layer 204 on the rear side thereof.

In the exemplary embodiment, the adhesive and adhesive layers 190A, 190B and 204 have the particular characteristics and configurations described below (relating to adhesive shear strength, pull-off strength, layer thickness).

Furthermore, in an exemplary embodiment, adhesive layers 190A and 190B each have an area (mm$^2$) to adhesive shear strength (kPa) ratio of about 100 mm$^2$/kPa to about 180 mm$^2$/kPa, which range includes an area (mm$^2$) to adhesive shear strength (kPa) ratio of 104 determined by the present inventors to be optimal for dry skin and an area (mm$^2$) to adhesive shear strength (kPa) ratio of 176 determined by the present inventors to be optimal for oily skin. Adhesive layers 190A and 190B each have an area (mm$^2$) to pull-off strength (kPa) ratio of about 40 mm$^2$/kPa to about 72 mm$^2$/kPa, which range includes an area (mm$^2$) to pull-off strength (kPa) ratio of 45.6 determined by the present inventors to be optimal for dry skin and an area (mm$^2$) to pull-off strength (kPa) ratio of 68.4 determined by the present inventors to be optimal for oily skin. Also, the thickness of adhesive layers 190A and 190B is ≥0.5 mm and ≤1.0 mm (for optimal adhesive shear strength), because cheek attachment portions 188A and 188B are structured to contact portions of the patient's face which tend to have a lower concentration of oil.

Also in the exemplary embodiment, adhesive layer 204 has an area (mm$^2$) to adhesive shear strength (kPa) ratio of about 32 mm$^2$/kPa to about 68 mm$^2$/kPa, which range includes an area (mm$^2$) to adhesive shear strength (kPa) ratio of 37 determined by the present inventors to be optimal for dry skin and an area (mm$^2$) to adhesive shear strength (kPa) ratio of 63 determined by the present inventors to be optimal for oily skin. Adhesive layer 204 has an area (mm$^2$) to pull-off strength (kPa) ratio of about 10 mm$^2$/kPa to about 30 mm$^2$/kPa, which range includes an area (mm$^2$) to pull-off strength (kPa) ratio of 6.2 determined by the present inventors to be optimal for dry skin and an area (mm$^2$) to pull-off strength (kPa) ratio of 24.3 determined by the present inventors to be optimal for oily skin. Also, the thickness of each of adhesive layer 204 has is ≥0.5 mm and ≤1.0 mm (for optimal adhesive shear strength), because first side region 154, and second side region 156 are structured to contact portions of the patient's face (cheek) which tend to have a lower concentration of oil (as compared to the lower lip/mouth/chin region).

In addition, in the exemplary embodiment, adhesive layers 164A and 164B each have an area (mm$^2$) to adhesive shear strength (kPa) ratio of about 5 mm$^2$/kPa to about 13 mm$^2$/kPa, which range includes an area (mm$^2$) to adhesive shear strength (kPa) ratio of 6.83 determined by the present inventors to be optimal for dry skin and an area (mm$^2$) to adhesive shear strength (kPa) ratio of 11.5 determined by the present inventors to be optimal for oily skin. Adhesive layers 164A and 164B each have an area (mm$^2$) to pull-off strength (kPa) ratio of about 2 mm$^2$/kPa to about 6 mm$^2$/kPa, which range includes an area (mm$^2$) to pull-off strength (kPa) ratio of 3 determined by the present inventors to be optimal for dry skin and an area (mm$^2$) to pull-off strength (kPa) ratio of 4.5 determined by the present inventors to be optimal for oily skin. Also, the thickness of each of adhesive layers 164A and 164B is ≥0.1 mm and ≤0.5 mm (for optimal adhesive shear strength), because nose bridge portion 198 structured to contact portions of the patient's face which tend to have a higher concentration of oil.

Moreover, in the exemplary embodiment, adhesive layers 190A, 190B and 204 each have a pull-off strength value throughout that is ≤40 kPa ("pull-off strength limit value") to prevent damage to aged, sensitive and/or medically affected (e.g., diabetes, skin disease) skin. Also in the exemplary embodiment, adhesive layers 190A, 190B and 204 each have a suggested adhesive shear strength value throughout (based on the analysis of scientific skin mechanics literature) that is ≤27 kPa ("adhesive shear strength limit value") to prevent damage to aged, sensitive and/or medically affected (e.g., diabetes, skin disease) skin. In an alternative embodiment, adhesive layers 190A, 190B and 204 each have a suggested adhesive shear strength value throughout (based on the analysis of scientific skin mechanics literature) that is ≤18 kPa. Furthermore, in the exemplary embodiment, adhesive layers 190A, 190B and 204 each have a suggested peel adhesion value of 0.15-0.2 N mm$^{-1}$ to avoid pain (it has been determined that beyond this limit is where persons experience pain from removal of adhesive materials).

Figure 7A:
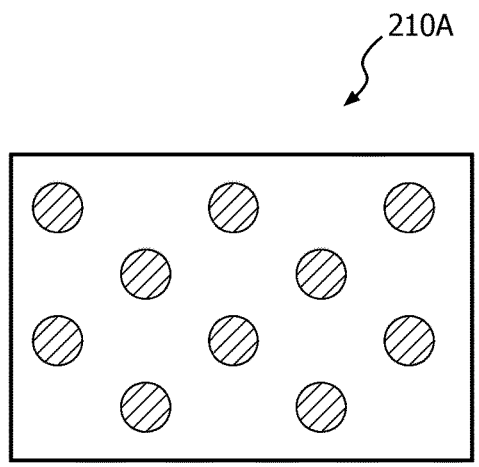
FIGS. 7A-7D are schematic representations of a number of adhesive deposition patterns (regular and repeating) that may be used in any of the adhesive layers described herein.
Figure 7B:
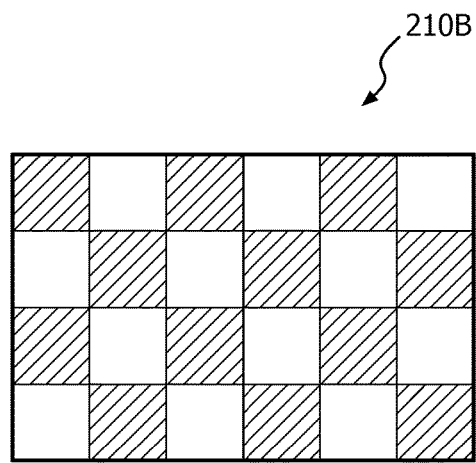
Figure 7C:
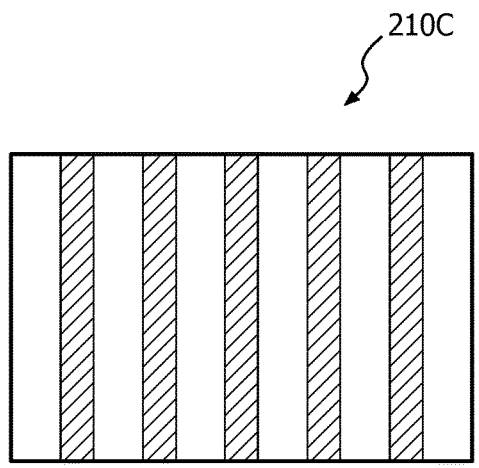
Figure 7D:
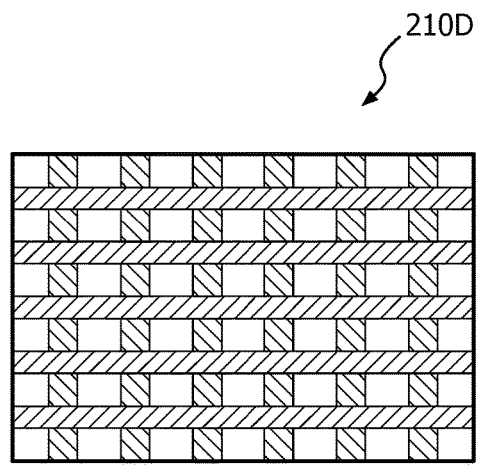

FIGS. 7A-7D are schematic representations of a number of adhesive deposition patterns (regular and repeating) that may be used in any of the adhesive layers described herein. The adhesive deposition patterns are each configured to allow for the efficient and optimal transfer of air/moisture to/from the skin. FIG. 7A shows a pattern 210A which comprises a plurality of rounded adhesive dots/spots that are spaced about the surface on which they are provided. FIG. 7B shows a pattern 210B which is in the form of a checkerboard pattern comprising a plurality of square adhesive deposits that are spaced about the surface on which they are provided. FIG. 7C shows a pattern 210C which comprises a plurality of generally parallel adhesive strips that are spaced along the surface on which they are provided. In one embodiment, the pitch (i.e., spacing) of the strips is such that the strips are spaced about 50 to 500 μm from one another. Finally, FIG. 7D shows a pattern 210D which comprises a plurality of adhesive strips that are provided in an overlapping mesh/grid pattern.

In one or more particular exemplary embodiments, nasal sealing cover 16, nasal mask portion 64, nasal sealing cover 110, cushion 146, or attachment pad 180 may have a stacked structure that includes a silicone base with a hydrophilic silicone layer provided on the silicone base, wherein the adhesive patterns shown in any of FIGS. 7A-7D are applied to the hydrophilic silicone layer. The present inventors have found that such a stacked structure improves water permeability and overcomes problems with moisture accumulation. Suitable hydrophilic silicone for the hydrophilic silicone layer is described in PCT application publication no. WO2013/001438, WO2013/001487, and WO2013/001506, the contents of each of which are incorporated herein by reference.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device structured to deliver a flow of breathing gas to an airway of a patient, comprising:

a member structured to contact and adhere to a face of the patient responsive to the patient interface device being donned by the patient, the member having a contact surface including a base region, an apex region located opposite the base region, a first side region, and a second side region located opposite the first side region, the member having an adhesive layer provided on the contact surface, wherein the adhesive layer has a pull-off strength limit value throughout the adhesive layer that is ≤40 kPa and an adhesive shear strength limit value throughout the adhesive layer that is ≤27 kPa, wherein a first thickness of the adhesive layer in the base region is ≥0.1 mm and ≤0.5 mm and wherein a second thickness of the adhesive layer in each of the apex region, the first side region and the second side region is ≥0.5 mm and ≤1.0 mm.

2. The patient interface device according to claim 1, wherein the adhesive layer has an area ($mm^2$) to adhesive shear strength (kPa) ratio of about 140 $mm^2$/kPa to about 270 $mm^2$/kPa and an area ($mm^2$) to pull-off strength (kPa) ratio of about 60 $mm^2$/kPa to about 105 $mm^2$/kPa.

3. The patient interface device according to claim 1, wherein the member is a nasal mask portion structured to sealingly cover a nose of the patient, the patient interface device further comprising a hollow delivery tube portion fluidly connected to and extending from a top of the nasal mask portion, and a forehead support portion coupled to a distal end of the delivery tube portion, wherein a second adhesive layer is provided on a rear surface of the forehead support portion, wherein the second adhesive layer has a pull-off strength limit value throughout the second adhesive layer that is ≤40 kPa and an adhesive shear strength limit value throughout the second adhesive layer that is that is ≤27 kPa.

4. The patient interface device according to claim 3, wherein the adhesive layer has an area ($mm^2$) to adhesive shear strength (kPa) ratio of about 110 $mm^2$/kPa to about 200 $mm^2$/kPa and an area ($mm^2$) to pull-off strength (kPa) ratio of about 45 $mm^2$/kPa to about 80 $mm^2$/kPa, and wherein the second adhesive layer has an area ($mm^2$) to adhesive shear strength (kPa) ratio of about 100 $mm^2$/kPa to about 185 $mm^2$/kPa and an area ($mm^2$) to pull-off strength (kPa) ratio of about 40 $mm^2$/kPa to about 75 $mm^2$/kPa.

5. The patient interface device according to claim 1, wherein the member is a nasal cushion structured to contact a nose of the patient and deliver the flow of breathing gas to the nose, wherein the patient interface device further comprises a nasal sealing cover coupled to the nasal cushion, the nasal sealing cover surrounding and enveloping a portion of the nasal cushion contacting the nose.

6. The patient interface device according to claim 5, wherein the adhesive layer has an area ($mm^2$) to adhesive shear strength (kPa) ratio of about 140 $mm^2$/kPa to about 270 $mm^2$/kPa and an area ($mm^2$) to pull-off strength (kPa) ratio of about 60 $mm^2$/kPa to about 105 $mm^2$/kPa.

7. The patient interface device according to claim 5, wherein the nasal cushion is a pillows style nasal cushion having a plurality of nasal prongs, wherein the nasal sealing cover surrounds and envelops the nasal prongs.

8. The patient interface device according to claim 5, further comprising a nasal shell member structured to match a shape of and overlay and receive therein the nasal sealing cover, the nasal shell member having one or more attachment members structured to receive a strap member of a headgear component.

9. The patient interface device according to claim 5, further comprising a delivery conduit member fluidly coupled to the nasal cushion, the delivery conduit member having a U-shaped bend portion structured to fit over and behind an ear of the patient responsive to the patient interface device being donned by the patient.

10. The patient interface device according to claim 1, wherein the member is a mask having a cushion, the contact surface being part of the cushion, wherein the adhesive layer comprises a first adhesive portion provided in the base region, a second adhesive portion provided in the first side region, a third adhesive portion provided in the second side region, and a fourth adhesive portion (164A, 164B) provided in the apex region, wherein the first adhesive portion has an area ($mm^2$) to adhesive shear strength (kPa) ratio of about 10 $mm^2$/kPa to about 25 $mm^2$/kPa and an area ($mm^2$) to pull-off strength (kPa) ratio of about 4 $mm^2$/kPa to about 12 $mm^2$/kPa, wherein the second and third adhesive portions each have an area ($mm^2$) to adhesive shear strength (kPa) ratio of about 5 $mm^2$/kPa to about 15 $mm^2$/kPa and an area ($mm^2$) to pull-off strength (kPa) ratio of about 2 $mm^2$/kPa to about 7 $mm^2$/kPa, and wherein the fourth adhesive portion has an area ($mm^2$) to adhesive shear strength (kPa) ratio of about 5 $mm^2$/kPa to about 13 $mm^2$/kPa and an area ($mm^2$) to pull-off strength (kPa) ratio of about 2 $mm^2$/kPa to about 6 $mm^2$/kPa.

11. The patient interface device according to claim 1, wherein the member is a mask having a cushion, the contact surface being part of the cushion, wherein the adhesive layer comprises a first and second adhesive portions provided on opposite sides of the base region at points that are immediately adjacent to the first side region and the second side region, respectively, and a third adhesive portion provided on the apex region spanning from one side to the other of the apex region through a middle of the apex region.

12. The patient interface device according to claim 1, wherein the member is a mask having a cushion, the contact surface being part of the cushion, wherein the adhesive layer comprises a first and second adhesive portions provided on opposite sides of the base region at points that are immediately adjacent to the first side region and the second side region, respectively, and third and fourth adhesive portions are provided on the first side region and the second side region, respectively, immediately adjacent to the apex region.

13. The patient interface device according to claim 1, wherein the adhesive layer is provided in a regular pattern selected from a group consisting of a plurality of rounded and spaced dots, a checkerboard pattern of generally parallel strips, and a plurality of strips provided in an overlapping mesh/grid pattern.

14. The patient interface device according to claim 1, wherein the member comprises a stacked structure having a silicone base with a hydrophilic silicone layer provided on the silicone base, wherein the adhesive layer is provided on the hydrophilic silicone layer.

15. The patient interface device according to claim 1, wherein the adhesive layer has a peel adhesion value throughout the adhesive layer of 0.15-0.2 N $mm^{-1}$.

16. A patient interface device structured to deliver a flow of breathing gas to an airway of a patient, comprising:

a nasal cushion structured to contact a nose of the patient and deliver the flow of breathing gas to the nose;

an attachment member coupled to and surrounding at least a portion of the nasal cushion, the attachment member being structured to contact and adhere to a face of the patient responsive to the patient interface device being donned by the patient, the attachment member having a contact surface and an adhesive layer provided on the contact surface, wherein the adhesive layer has a pull-off strength limit value throughout the adhesive layer that is ≤40 kPa and an adhesive shear strength limit value throughout the adhesive layer that is ≤27 kPa, wherein a first thickness of the adhesive layer in a first region thereof is ≥0.1 mm and ≤0.5 mm and wherein a second thickness of the adhesive layer in a second region thereof is ≥0.5 mm and ≤1.0 mm.

17. The patient interface device according to claim 16, wherein the nasal cushion is a pillows style nasal cushion having a plurality of nasal prongs, wherein the attachment member is a nasal sealing cover that surrounds and envelops the nasal prongs.

18. The patient interface device according to claim 16, wherein the attachment member has a central body, a first arm member extending from a first side of the central body and a second arm member extending from a second side of the central body, the first arm member having a first cheek attachment portion at a distal end thereof, the second arm member having a second cheek attachment portion at a distal end thereof, wherein the adhesive layer comprises a first adhesive portion provided on a rear of the first cheek attachment portion, and a second adhesive portion provided on a rear of the second cheek attachment portion, wherein the attachment member further includes a nasal attachment member that extends from a top portion of the central body that together with the central body defines a nasal orifice, wherein the adhesive layer comprises a third adhesive portion provided on a rear of the nasal attachment member.

19. The patient interface device according to claim 18, wherein the first region includes the third adhesive portion and the second region includes the first and second adhesive portions.

20. The patient interface device according to claim 19, wherein the first and second adhesive portions each have an area ($mm^2$) to adhesive shear strength (kPa) ratio of about 100 $mm^2$/kPa to about 180 $mm^2$/kPa and an area ($mm^2$) to pull-off strength (kPa) ratio of about 40 $mm^2$/kPa to about 72 $mm^2$/kPa, and wherein the third adhesive portion has an area ($mm^2$) to adhesive shear strength (kPa) ratio of about 32 $mm^2$/kPa to about 68 $mm^2$/kPa and an area ($mm^2$) to pull-off strength (kPa) ratio of about 10 $mm^2$/kPa to about 30 $mm^2$/kPa.

* * * * *